(12) United States Patent
Hutchins, III et al.

(10) Patent No.: US 9,492,266 B2
(45) Date of Patent: Nov. 15, 2016

(54) URETERAL STENT DRUG DELIVERY DEVICE, KIT, AND METHOD

(75) Inventors: Burleigh M. Hutchins, III, Upton, MA (US); Cheryl Larrivee-Elkins, Framingham, MA (US); Heejin Lee, Arlington, MA (US); Jim Boyko, Attleboro, MA (US)

(73) Assignee: TARIS Biomedical LLC, Lexington, MA (US)

( * ) Notice: Subject to any disclaimer, the term of this patent is extended or adjusted under 35 U.S.C. 154(b) by 58 days.

(21) Appl. No.: 13/813,973

(22) PCT Filed: Aug. 5, 2011

(86) PCT No.: PCT/US2011/046843
§ 371 (c)(1),
(2), (4) Date: Feb. 4, 2013

(87) PCT Pub. No.: WO2012/019155
PCT Pub. Date: Feb. 9, 2012

(65) Prior Publication Data
US 2013/0158675 A1   Jun. 20, 2013

Related U.S. Application Data

(60) Provisional application No. 61/371,139, filed on Aug. 5, 2010.

(51) Int. Cl.
*A61F 2/04* (2013.01)
*A61F 2/06* (2013.01)
*A61M 27/00* (2006.01)
*A61M 25/00* (2006.01)

(52) U.S. Cl.
CPC ............ *A61F 2/04* (2013.01); *A61M 25/0041* (2013.01); *A61M 27/008* (2013.01); *A61M 25/0017* (2013.01); *A61M 2025/0057* (2013.01); *Y10T 29/49826* (2015.01)

(58) Field of Classification Search
USPC ......................... 623/1.42–1.46, 23.64–23.71
See application file for complete search history.

(56) References Cited

U.S. PATENT DOCUMENTS

| | | |
|---|---|---|
| 4,871,542 A | 10/1989 | Vilhardt |
| 6,368,356 B1 | 4/2002 | Zhong et al. |
| 6,656,162 B2 | 12/2003 | Santini, Jr. et al. |

(Continued)

OTHER PUBLICATIONS

Krambeck, A.E., "A Novel Drug Eluting Ureteral Stent: A Prospective, Randomized, Multicenter Clinical Trial to Evaluate the Safety and Effectiveness of a Ketorolac Loaded Ureteral Stent", 2010 American Urological Association Education and Research, Inc. vol. 183, 1037-1043, Mar. 2010.

(Continued)

*Primary Examiner* — Yashita Sharma
(74) *Attorney, Agent, or Firm* — Sutherland Asbill & Brennan LLP

(57) ABSTRACT

Ureteral stent devices having improved drug delivery capabilities are provided. The ureteral stent device includes a ureteral stent comprising two opposed ends, and a drug delivery component associated with at least one end of the ureteral stent. The drug delivery component includes a drug housing defining a drug reservoir containing a drug, wherein the drug housing is configured to release the drug in-vivo.

36 Claims, 10 Drawing Sheets

(56) References Cited

U.S. PATENT DOCUMENTS

| | | |
|---|---|---|
| 6,949,125 B2 | 9/2005 | Robertson |
| 7,862,552 B2 | 1/2011 | McIntyre et al. |
| 8,167,836 B2 | 5/2012 | Lee et al. |
| 8,182,464 B2 | 5/2012 | Lee et al. |
| 8,343,516 B2 | 1/2013 | Daniel et al. |
| 2008/0004578 A1 | 1/2008 | Hixon et al. |
| 2008/0234659 A1 | 9/2008 | Cheng et al. |
| 2009/0171465 A1 | 7/2009 | Bucay-Couto et al. |
| 2009/0187254 A1 | 7/2009 | Deal et al. |
| 2009/0247992 A1 | 10/2009 | Shalon et al. |
| 2009/0292237 A1 | 11/2009 | Overstreet et al. |
| 2009/0312833 A1* | 12/2009 | Tittelbach ............... A61F 2/86  623/1.42 |
| 2010/0145467 A1 | 6/2010 | Davoudi et al. |
| 2010/0331770 A1 | 12/2010 | Lee et al. |
| 2011/0060309 A1 | 3/2011 | Lee et al. |
| 2011/0152839 A1 | 6/2011 | Cima et al. |
| 2011/0202036 A1 | 8/2011 | Boyko et al. |
| 2011/0218488 A1 | 9/2011 | Boyko et al. |
| 2013/0131637 A1 | 5/2013 | DiCesare et al. |

OTHER PUBLICATIONS

William N. Taylor et al., "Minimally Invasive Ureteral Stent Retrieval," The Journal of Urology, vol. 168, 2020-2023, Nov. 2002.

* cited by examiner

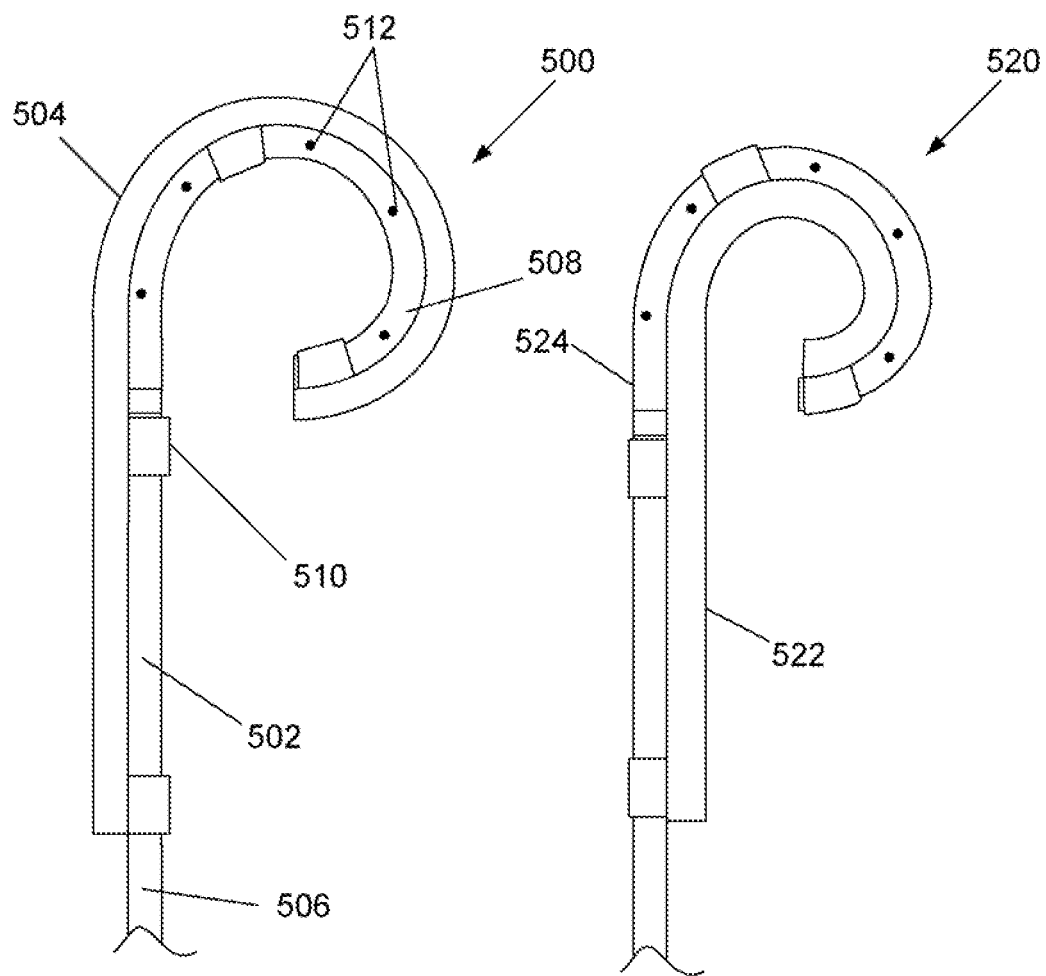

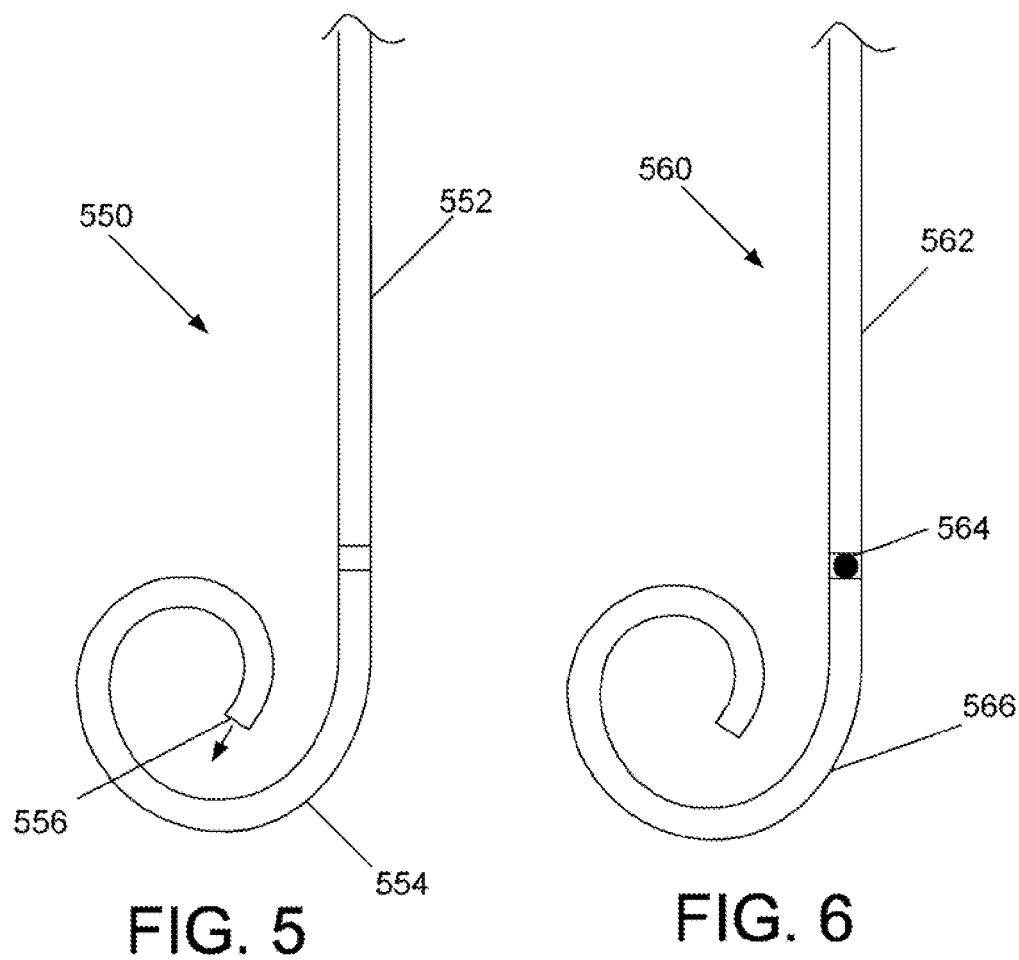

URETERAL STENT DRUG DELIVERY DEVICE, KIT, AND METHOD

CROSS-REFERENCES TO RELATED APPLICATIONS

The present application is a national phase entry of PCT Patent Application No. PCT/US2011/046843, filed on Aug. 5, 2011, designating the United States of America, and claims the benefit of U.S. Provisional Application No. 61/371,139, filed on Aug. 5, 2010, which is incorporated herein by reference in its entirety.

BACKGROUND

Ureteral stents are commonly used for the treatment of renal diseases and conditions, such as kidney stones. Once implanted, the stent extends through the ureter from the kidney to the bladder, maintaining patency of the ureter and permitting drainage. The placement of a ureteral stent often causes side effects for the patient, such as bladder pain, discomfort, urinary urgency, or urinary frequency. Currently, these side effects are treated with oral therapies, such as narcotics, alpha blockers, and antimuscarinics. Efficacy is variable, and treatment-limiting side effects occur. Some drug-coated ureteral stents have been employed for local drug delivery, but such known stents generally have a relatively small drug payload and cannot deliver an effective amount of drug in a controlled manner over an extended period of time.

For example, U.S. Pat. No. 7,862,552 to McIntyre et al. discloses a ureteral stent having a drug-eluting region. The drug-eluting region comprises a drug contained within a polymeric matrix. Although such drug-eluting ureteral stents have demonstrated some improvements in reducing pain associated with the use of the ureteral stent in a subset of patient populations, in clinical trials, one such drug-eluting stent "did not demonstrate a clear advantage in reducing the number of unscheduled physician contacts, early stent removals, pain medication changes, or patient assessed pain [Visual Analog Score]." See Krambeck et al.: A Novel Drug Eluting Ureteral Stent: A Prospective, Randomized, Multicenter Clinical Trial to Evaluate the Safety and Effectiveness of Ketorolac Loaded Ureteral Stent; *The Journal of Urology*; March 2010; 183: 1037-43.

It therefore would be desirable provide improved ureteral stents and methods for treating pain and other side effects associated with the implantation of a ureteral stent in patients. It also would be desirable to delivery a drug to the bladder for any other treatment purpose in conjunction with the deployment of a ureteral stent in a patient.

SUMMARY

Ureteral stent devices having improved drug delivery capabilities are provided. In one aspect, an implantable medical device is provided that includes a ureteral stent comprising two opposed ends, and a drug delivery component associated with at least one end of the ureteral stent. The drug delivery component includes a drug housing defining a drug reservoir containing a drug, wherein the drug housing is configured to release the drug in-vivo.

In another aspect, a method of delivering a drug from a ureteral stent device is provided. The method includes implanting a ureteral stent device in a ureter of a patient, the ureteral stent device including a drug delivery component comprising a drug housing defining a drug reservoir containing a drug; and releasing the drug from the drug delivery component into the patient's body.

In yet another aspect, a methods is provided for treating one or more side effects associated with placement of the ureteral stent in the body. The method includes implanting a ureteral stent device in a ureter of a patient, the ureteral stent device including a drug delivery component comprising a drug housing defining a drug reservoir containing a drug; and releasing the drug from the ureteral stent device into the patient. The drug may be selected, for example, from the group consisting of: a local anesthetic agent, an anti-muscarinic, an alpha-blocker, a narcotic, phenazopyridine and combinations thereof.

In still another aspect, a medical procedure kit is provided. The medical procedure kit includes a ureteral stent having a bladder end and a kidney end; and at least one drug delivery portion with means for attachment to one of the ends of the ureteral stent in-vivo, the drug delivery portion comprising a drug housing defining a drug reservoir containing a drug.

BRIEF DESCRIPTION OF THE DRAWINGS

FIGS. 1-7 illustrate various examples of embodiments of ureteral stent devices configured for drug delivery.

DETAILED DESCRIPTION

Figure 3:
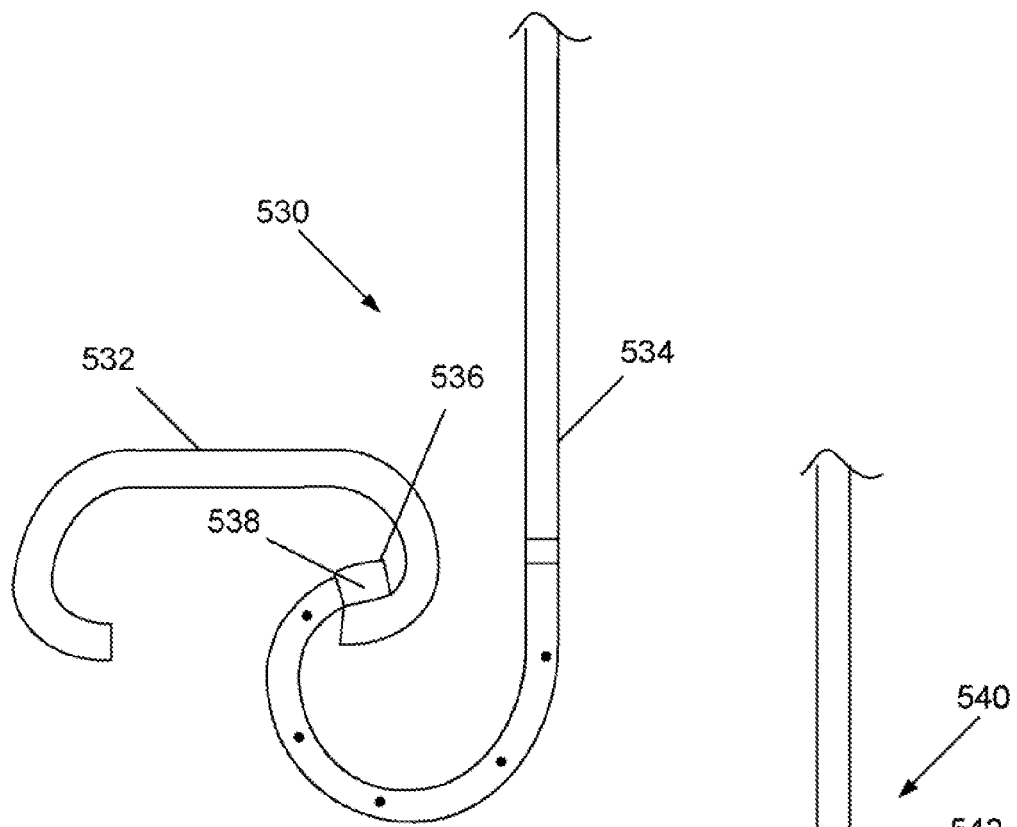

Described herein are embodiments of an implantable ureteral stent device configured for drug delivery. The ureteral stent device can be implanted in a ureter with its two opposing end portions residing in the kidney and the bladder. Once implanted, the ureteral stent device holds the ureter open and may communicate fluid (e.g., urine) from the kidney to the bladder. The device also delivers drug locally or regionally, such as to the bladder, kidney, or ureter. Methods of local delivery of drug also are disclosed.

The ureteral stent device generally includes a ureteral stent portion and a drug delivery portion. The stent portion of the device is sized and shaped to extend though the ureter from the kidney to the bladder. The stent includes an elongated central body and two opposed ends, including a bladder-residing end and a kidney-residing end. When the stent is implanted, the kidney-residing end is positioned in the kidney and the bladder-residing end is positioned in the bladder, with the central body extending through the ureter between the two ends. Each of the ends may be associated with an opening that is in fluid communication with an internal lumen in the elongated central body. The openings and the internal lumen enable fluid (e.g., urine) to flow from the kidney through the ureter to the bladder.

The ends of the ureteral stent device can have a range of configurations. In some embodiments, the ends are straight. In other embodiments, one or both of the ends have curved or coiled configurations that facilitate retaining the stent end in the body. Such curved or coiled ends are commonly referred to in the art as "pigtails".

The stent device also includes at least one drug delivery portion associated with the ureteral stent portion, such as with one of the stent ends. In particular embodiments, the drug delivery portion is positioned on the bladder-residing end to deliver drug locally to the bladder, although the kidney-residing end also may be associated with a drug delivery portion, or both ends may be associated with separate drug delivery components, regardless of whether the stent ends are straight or pigtailed. The drug delivery portion also may extend along all or some of the central body of the ureteral stent portion in some embodiments.

The drug delivery portion generally includes a drug housing defining a drug reservoir and a drug contained within the drug reservoir. The term "reservoir" as used herein refers to a hollow space, such as a central lumen or annular space, bounded at least in part by a wall, suitable for receiving a drug payload for dispensing, e.g., suitable for being filled by a drug. The drug housing is configured to release the drug at the implantation site. One embodiment of a drug housing, briefly described, includes a flexible tube loaded with a row or line of solid drug tablets. The tube may be formed from a water-permeable material so that water can enter the tube to solubilize the drug. The solubilized drug may be released via osmotic pump action and/or by diffusion. In one embodiment in which the drug is released via osmotic pressure, the drug housing includes a release aperture and the drug is in a highly water soluble form. An example tube and drug combination contemplated for such release is a silicone tube loaded with a highly water soluble form of lidocaine, such as lidocaine hydrochloride monohydrate. In one embodiment in which the drug is released via diffusion, the drug housing is permeable to the solubilized drug. An example tube and drug combination contemplated for such release is a silicone tube loaded with a form of lidocaine having a low water solubility, such as lidocaine base.

The drug delivery portion can have a range of configurations, including a configuration described in one the following U.S. patent applications, each of which is incorporated by reference herein: U.S. Application Publication No. 2009-0149833; U.S. Application Publication No. 2010-0331770; U.S. Application Publication No. 2010-0330149, U.S. Application Publication No. 2011-0060309; and U.S. Application Publication No. 2011-0152839.

The ureteral stent portion and the drug delivery portion may be formed separately and attached to each other, either before or after insertion, such as with adhesive, a magnet, a suture, or other connection means. The two portions also may be partially or completely formed integrally as a single unit.

Particular embodiments of the ureteral stent drug delivery portion are illustrated in FIGS. 1-7. FIGS. 1 and 2 illustrate embodiments of ureteral stent devices 500, 520 wherein the drug delivery portion 504, 522 is parallel and adjacent to the stent portion 502 along one of its ends, such as at the bladder-residing end 508 of the stent portion 502. The drug delivery component 504, 522 may tend to lie inside (FIG. 1) or outside (FIG. 2) of the stent end when in the pig-tail configuration. By way of example, the bladder-residing end 508 is shown in a pig-tail configuration. It may be desirable for the drug delivery portion to lie inside the stent end to reduce the risk of the drug delivery portion contacting the implantation site. Alternatively, the drug delivery component may lie on the side of the stent portion (i.e., neither on the inside nor the outside of the stent portion) such that the curvature of the drug delivery portion substantially mimics the curvature of pigtail of the stent portion. In some embodiments, the drug delivery portion 504 may extend along only a portion of the length of the stent portion 502. For example, the drug delivery portion 504, may extend only along the pigtail portion at the bladder-residing end 506. Alternatively, the drug delivery portion 504 may also extend along a portion of the elongate central body 506 of the stent portion 502 as illustrated in FIG. 1. In some embodiments, the drug delivery portion 504 may be attached to the stent portion 502 by one or more attaching elements, such as sleeves 510 that encircle the stent portion 502. Other types of attaching elements may also be used. In certain embodiments, the attaching elements (e.g., sleeves 510) may be positioned at locations along the length of the drug delivery portion 504 that will not block the openings 512 that allow urine to pass into or out of the stent portion 502 when the drug delivery portion 504 is attached to the stent portion 502 at it intended attachment location (e.g., at the bladder-residing end 508 of the stent portion 502). Different embodiments and configurations for the drug delivery portion 504 are described in greater detail subsequently.

FIGS. 3 through 7 illustrate additional embodiments of ureteral stent devices wherein the drug delivery portion is attached to a distal tip of the ureteral stent portion. For example, an end of the drug delivery portion may be attached to a distal tip of the ureteral stent portion as shown, although other points on the drug delivery portion can be attached to this or other points on the ureteral stent portion.

Figure 4:
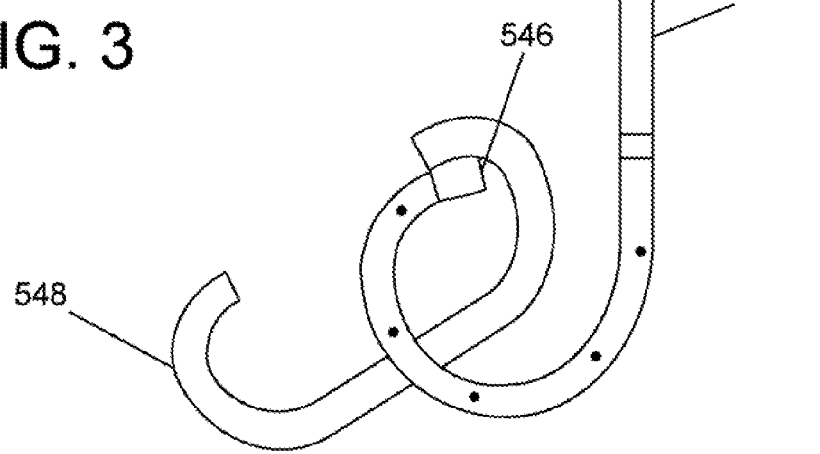

The drug delivery portion may be separate, may be spaced apart, or may include a portion that extends away, from the ureteral stent portion, such that the drug delivery portion has increased exposure to the intended site of deployments, e.g., the bladder, as shown in FIGS. 3 and 4. The drug delivery portion may be movable between a deployment shape suited for deployment through a working channel of a deployment instrument and a retention shape, which may be coiled or curved. In some embodiments, the drug delivery portion may include a retention frame operable to cause the drug delivery component to assume the retention shape upon implantation. For example, as illustrated in FIGS. 3 and 4, the ureteral stent device 530, 540 may include a drug delivery portion 532, 548 that includes a portion that extends away from the stent portion 534, 542. The drug delivery portion 532 may be attached to the distal tip 536 of the stent portion 534, 542 by an attaching element, such as a sleeve 538 that encircle the stent portion 534. Other types of attaching elements may also be used.

The drug delivery portion also may extend from the ureteral stent along or from the stent's distal end, as shown in FIGS. 5-6. In some embodiments, the internal lumen through the ureteral stent portion terminates before the drug delivery portion begins, such that the exit opening for the internal lumen becomes positioned between the drug delivery portion and the ureteral stent portion as shown in FIG. 6. For example, as illustrated in FIG. 6, the device 560 may include an aperture 564 in the sidewall of the stent portion 562 at or proximal the end of the stent portion 562 which allows urine passing through the interior lumen of the stent portion 562 to exit through the sidewall of the stent instead of passing through the drug delivery portion 566. The drug delivery portion 566 may extend from the end of the stent portion 562 adjacent to the aperture 564. In some embodiments, the drug delivery portion 566 may form a pigtail such as is illustrated in FIG. 6.

In other embodiments, the internal lumen through the ureteral stent extends through the drug delivery portion or may be fluidly connected to an internal lumen passing through the drug delivery structure, such that the exit opening for the internal lumen becomes positioned at the distal end of the drug delivery portion, as shown in FIG. 5. For example, as illustrated in FIG. 5, the device 550 may include an internal lumen that passes through drug delivery portion 554 to fluidly connect an orifice 556 at an end of the drug delivery portion 554 to a lumen extending through the stent portion 552. In some embodiments, the drug delivery portion 554 may form a pigtail such as is illustrated in FIG. 5.

Figures 7A, 7B:
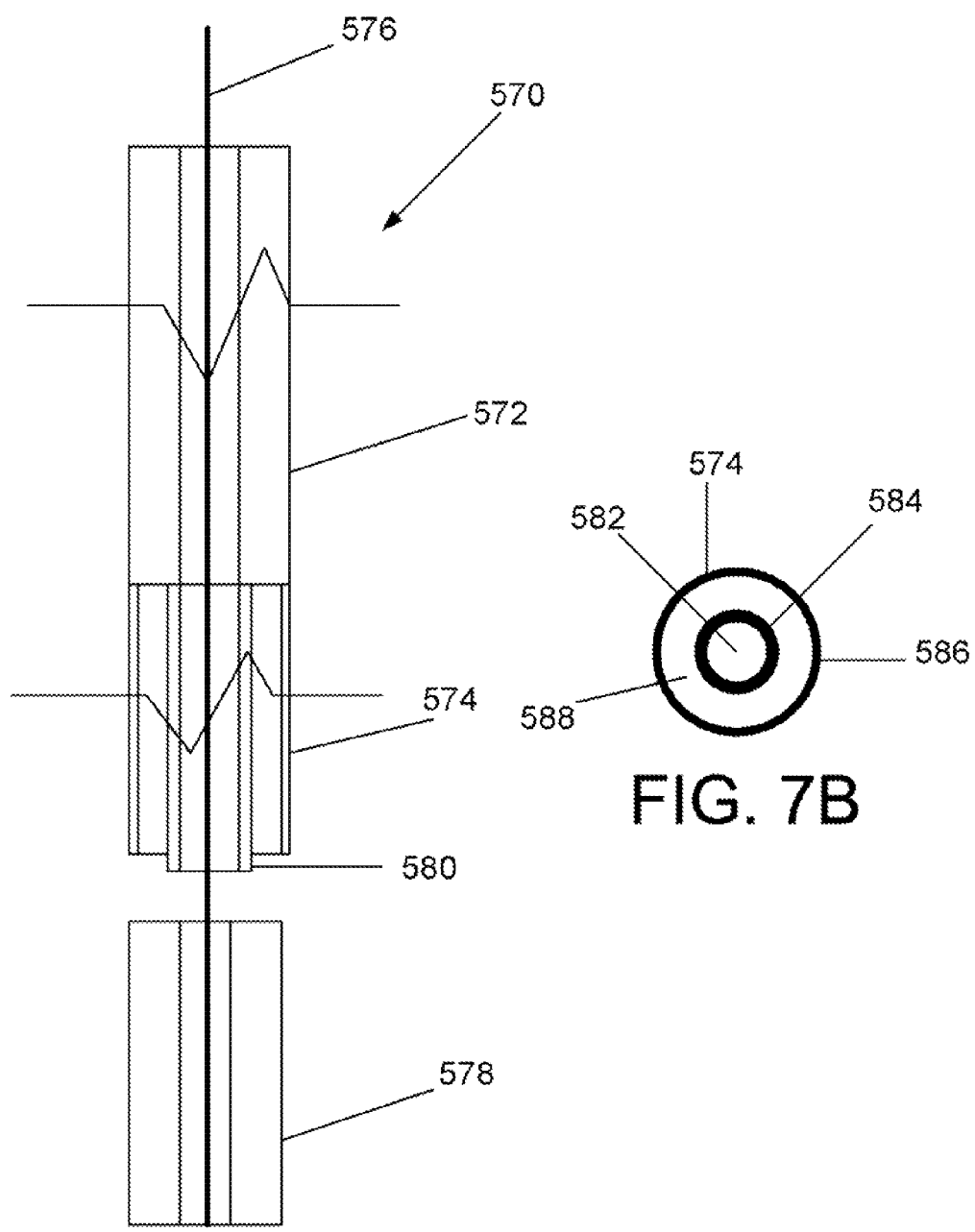

FIGS. 7A and 7B illustrate cross-sectional views of an embodiment of a ureteral stent. In the illustrated embodiment, both the drug delivery portion 574 and the ureteral stent portion 572 of device 570 have hollow interior lumens that align with each other, as shown in FIG. 7A, to form a single continuous lumen. As shown in FIG. 7B, the drug housing may have concentric inner wall 584 and outer wall 586 that define an annular shaped drug reservoir 588, with the interior lumen 582 running through its center. The drug delivery portion may be a separate component that is attached to the ureteral stent portion at its distal end, or the drug delivery portion may be at least partially integrally formed with the ureteral stent portion. The device 570 may include a rigid extension 580 extending from the distal end of the drug delivery portion 574 for interfacing with a pusher 578 when the device 570 is deployed into the ureteral lumen over a guidewire 576. The rigid extension 580 may be a portion of the inner wall 584 of the drug delivery portion 574 that extends beyond the drug reservoir 588 or it may be a separate and distinct component attached to the distal end of the drug delivery portion 574.

Figure 8A:
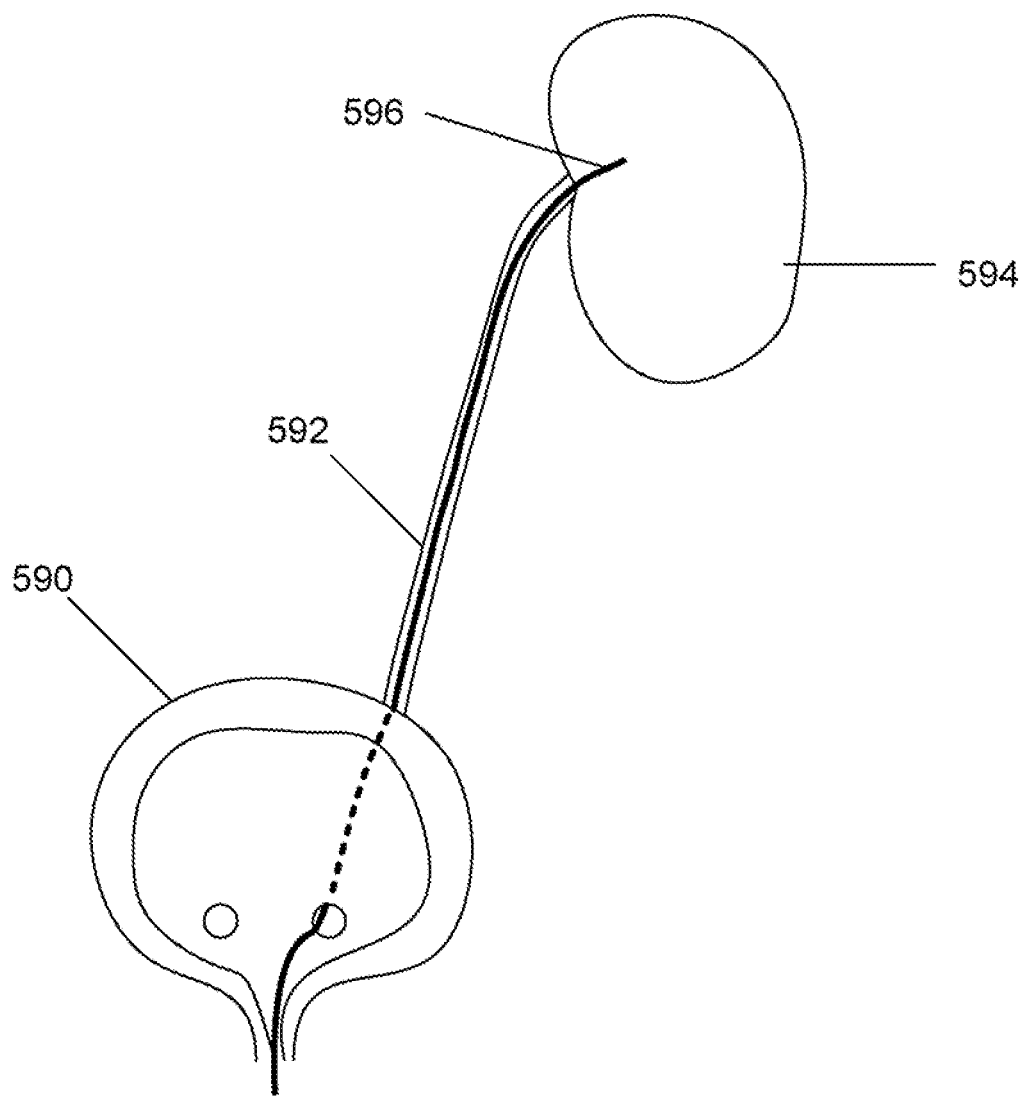
FIG. 8 illustrates deployment of a ureteral stent device over a guidewire.
Figure 8B:
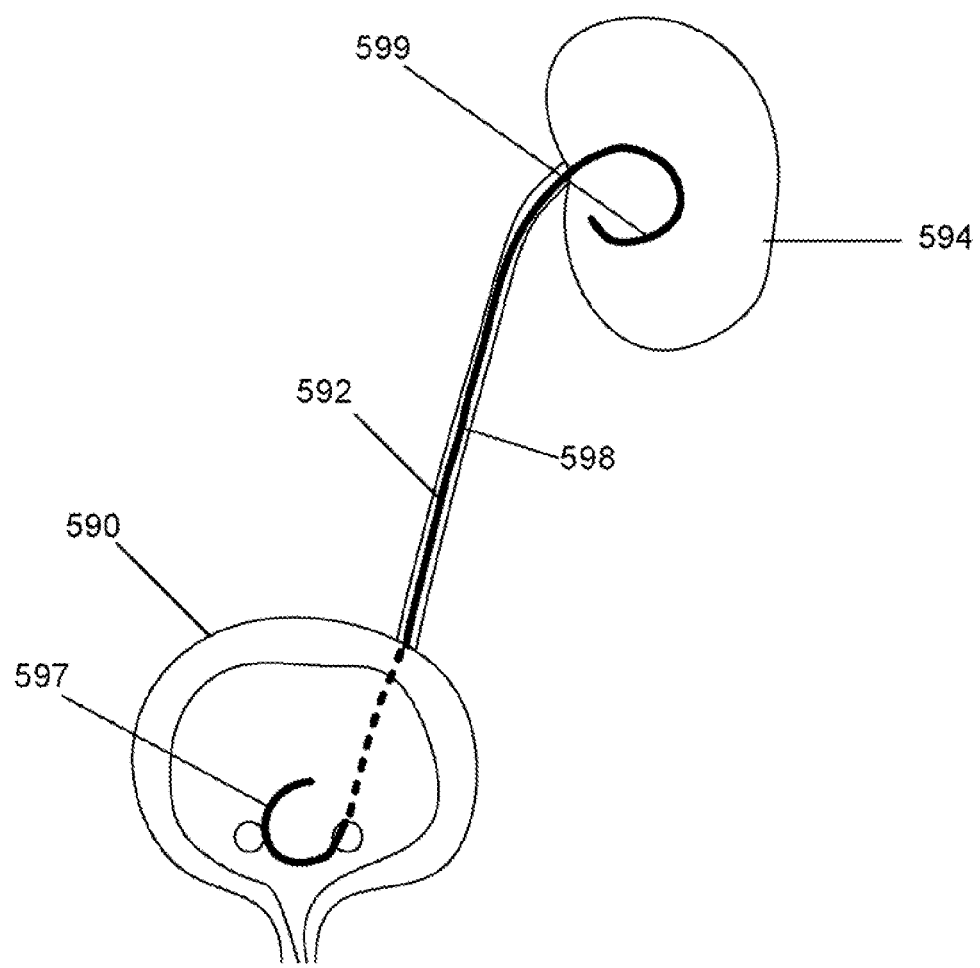

In various embodiments, the ureteral stent device can be implanted in various manners, such as by threading the device over a guidewire extending through the ureter. An example of such an implantation procedure is illustrated in FIGS. 8A and 8B. A guidewire 596 may be threaded through a ureter 592 as shown in FIG. 8A such that the guidewire 596 extends from the bladder 590 to the kidney 594. The device then may be threaded over the guidewire, either with or without the assistance of a ureteral access sheath and/or a pusher (stylet). The guidewire is then removed from the ureter, leaving the ureteral stent device in position. In embodiments in which the stent device includes pigtail ends, the ends may return as shown in FIG. 8B to retain the stent in position. The central lumen 598 of the stent portion may extend through ureter 529 providing a path for the flow of urine from the kidney 594 to the bladder 590. In one embodiment, one end of the stent forms a pigtail 599 within the kidney and the drug delivery portion 597 forms a pigtail shape within the bladder 590.

Figure 9:
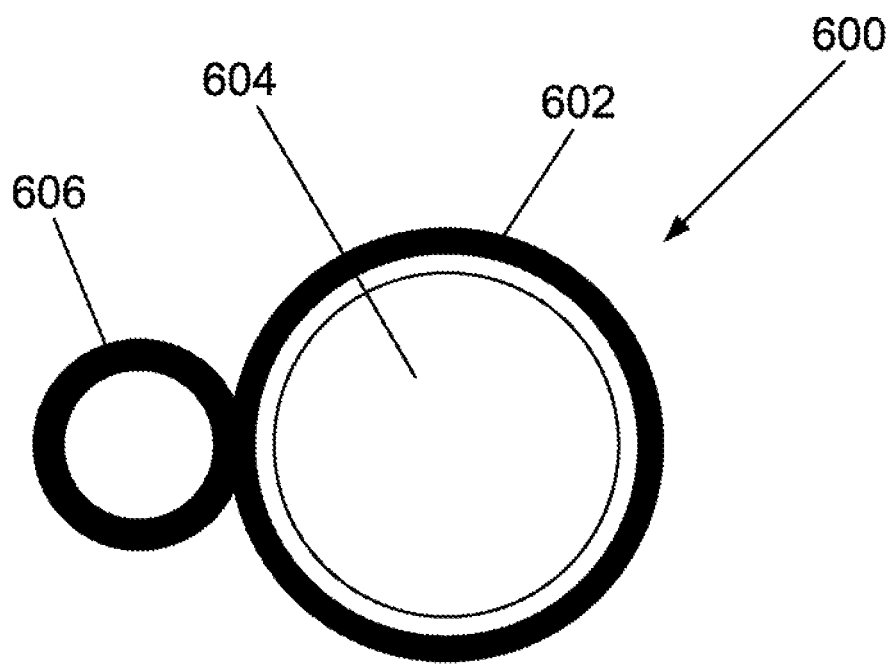
FIG. 9 illustrates an embodiment of a drug delivery portion of a ureteral stent device, the drug delivery portion having a guidewire lumen for deploying the ureteral stent device over a guidewire.

So that the ureteral stent device can be threaded over a guidewire, the device may include a guidewire lumen. In the embodiment of FIG. 7, the internal lumen that provides a path for urine flow after implantation also may serve as a guidewire lumen for threading the device over a guidewire during implantation. In other embodiments, the drug delivery portion may include a separate guidewire housing that defines a guidewire lumen, as shown in FIG. 9. The separate guidewire lumen permits threading the ureteral stent device over a guidewire, the ureteral stent portion passing over the guidewire through its internal lumen and the drug delivery portion passing over the guidewire through its guidewire lumen. In such an embodiment, the guidewire may pass through the exit opening at the distal end of the ureteral stent portion to reach the guidewire lumen of the drug delivery component. A pusher may be used to push the device over the guidewire lumen. As illustrated in FIG. 9, the drug delivery portion 600 may include a drug reservoir formed at least in part by an outer wall 602. A solid drug 604 may be contained within the drug reservoir. A guidewire lumen 606 may be provided outside the drug reservoir, for example, the guidewire lumen 606 may have a central axis extending parallel to the central axis of the drug reservoir as shown. In embodiments in which the drug delivery portion has a separate guidewire housing as shown in FIG. 9, the pusher may have an channel that accommodates the drug delivery portion so that the overall cross-section of the device can fit within a ureteral access sheath. In another embodiment, the guidewire lumen may be defined within the outer wall of the drug reservoir, for example, the guidewire lumen may be defined in part by the outer wall and in part by the solid drug formulation, which may for example include a flat or concave edge portion forming a gap between the solid drug formulation and the reservoir wall.

The ureteral stent device may be generally configured to reduce or avoid passage of the drug delivery portion into the ureter and to reduce or avoid contact of the drug delivery portion with the implantation site, such as the bladder wall. For example, the ureteral stent portion may be longer than a conventional ureteral stent. As another example, the ureteral stent portion may be broader than a convention stent along its end associated with (e.g., connected to) the drug delivery portion. The size and shape of the ureteral stent portion may otherwise accord with known ureteral stent configurations.

In some embodiments, the device may be deployed in a minimally invasive procedure, such as by implanting the device through the urethra into the ureter so that the drug delivery portion becomes implanted in the bladder, kidney or both. Once so implanted, the drug delivery portion can release one or more drugs over an extended period. The drug may be delivered locally to the bladder or kidney, or regionally to the implantation site, including the ureter. The drug may be released by osmotic pumping through an opening in the drug delivery portion, by diffusing through a surface of the drug delivery portion, by diffusing from an opening in the drug delivery portion, or a combination thereof. The drug release may be continuous and in accordance with a predefined release profile.

The drug can be delivered for the prophylaxis or treatment of one or more side effects associated with placement of the ureteral stent in the body, such as bladder pain, discomfort, urinary urgency, or urinary frequency. Examples of suitable drugs for such treatment include local anesthetic agents such as lidocaine, anti-muscarinics, alpha-blockers, narcotics, and phenazopyridine. Other drugs also can be delivered, such as for the treatment of kidney stones. The drug delivery component may release the drug continuously for an extended period. Other drugs and conditions can be treated with the device, as described in U.S. patent applications incorporated by reference herein.

The devices described herein provide local (and in some cases, regional) drug delivery in association with ureteral stent placement directly from the stent itself, as opposed to a separate device implanted in the kidney or bladder that may interfere with the implanted stent. Unlike known ureteral stents that deliver drugs, the present devices can deliver a larger drug payload without coating its exterior. Thus, one advantageously may avoid having the ureter directly contact a high concentration of drug in a drug coating. The interior of the ureteral stent also is beneficially left open for permitting passage of urine to the bladder.

Figure 10:
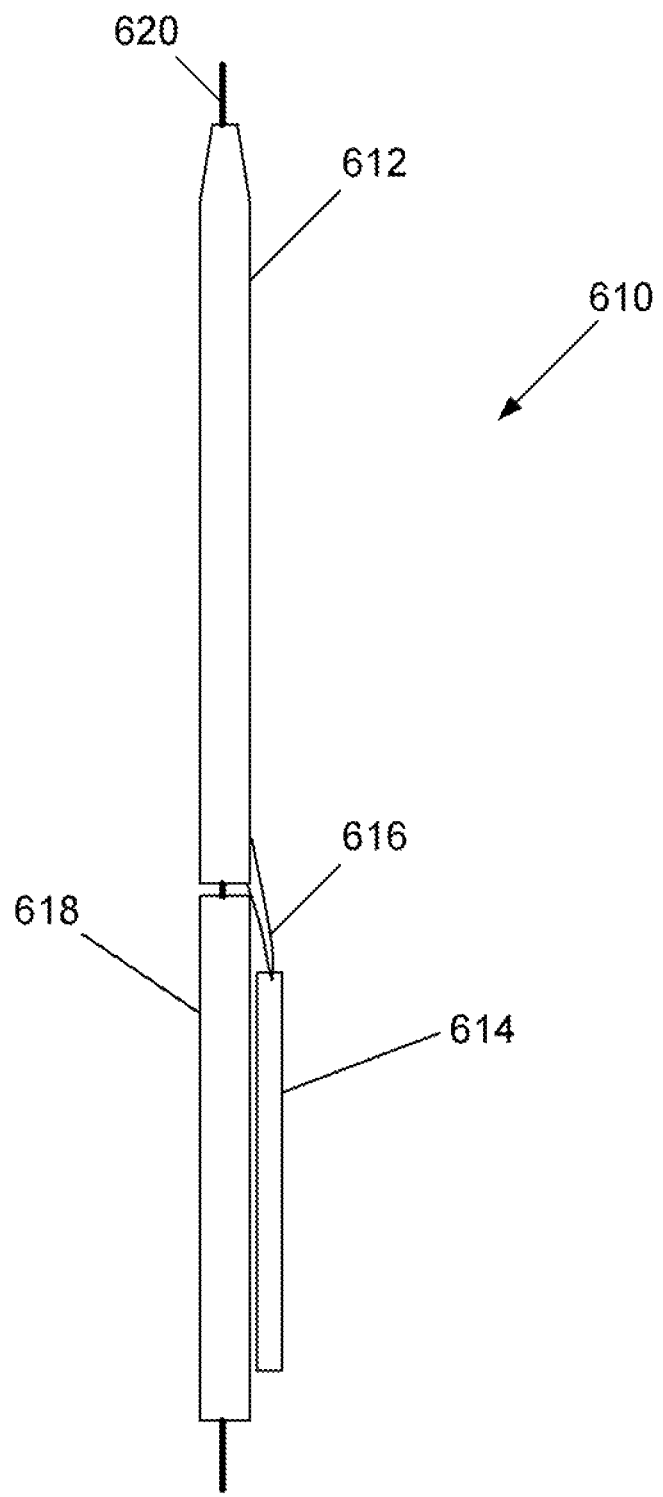
FIG. 10 is a plan view of an embodiment of a drug delivery portion tethered to a stent for deployment.

In other embodiments, the ureteral stent device may be any ureteral stent now known or later developed, and the ureteral stent may be attached to a separate drug delivery portion, either before or after the ureteral stent is implanted, such as using a suture or magnet. The separate drug delivery portion may be an embodiment of a device described in the U.S. patent applications incorporated by reference herein. For example, as illustrated in FIG. 10, the ureteral stent device 610 may include a stent portion 612 and a drug delivery portion 614 that is tethered to the stent portion 612 by a tether 616, such as a suture. The drug delivery portion 614 may be tethered to the bladder residing end of the stent portion 612 such that the drug delivery portion 614 will reside in the bladder when the device 610 is deployed. The device 610 may be configured such that the tether 616 will allow the drug delivery portion 614 be pulled behind the stent portion 612 (for example, the drug delivery portion 614 may be pulled beside the pusher 618) when the stent portion 612 is fed over the guidewire 620 during deployment.

Other implantable drug delivery portions also can be used. In one case, the separate drug delivery portion is deployed in the bladder after the ureteral stent is implanted, and then the drug delivery portion may be attached about the bladder end of the stent. In one such embodiment, the ureteral access sheath can be used as the deployment conduit for the drug delivery portion since the sheath is already in place for the stent insertion. So after removal of the dialator and guidewire follow stent placement, the drug delivery portion is deployed in the bladder through the access sheath.

Drug Delivery Portions

Drug delivery portions for ureteral stent devices are provided that can be deployed, or implanted, into the bladder for release of one or more drugs over an extended period. The devices and methods disclosed herein build upon those described in the U.S. patent applications identified above that are incorporated by reference herein.

The drug delivery device may be designed for deployment into and retention within the bladder. The drug delivery portion may be deployed through a deployment instrument, such as a catheter or cystoscope, positioned in the urethra, into the bladder. The drug delivery portion may be flexible so that the drug delivery portion can be deformed for insertion, yet once implanted the drug delivery portion may resist excretion in response to the forces of urination or other forces. In particular embodiments, an implantable drug delivery portion is loaded with one or more drugs in the form of a number of solid drug units, such as tablets or pellets. Advantageously, the drug loaded device in a preferred embodiment is flexible or deformable despite being loaded with solid drug, as each drug unit may be permitted to move with reference to adjacent drug units.

In particular embodiments, the drug delivery portion is small, such as small enough to be inserted through a deployment instrument extending through the urethra into the bladder. Such a device may be loaded with solid drug tablets that are substantially smaller than conventional drug tablets, and unlike conventional tablets the drug tablets also may constitute mostly drug and little or no excipients, so that the drug tablets contain a large amount of drug considering the tablet size. In particular embodiments, the drug delivery portion may deliver lidocaine or another cocaine analogue locally to the bladder over a relatively extended period for the treatment of a condition such as IC/PBS, neurogenic bladder, or pain such as post-operative pain.

The devices and methods disclosed herein may be adapted for use in humans, whether male or female, adult or child, or for use in animals, such as for veterinary or livestock applications.

Figure 11:
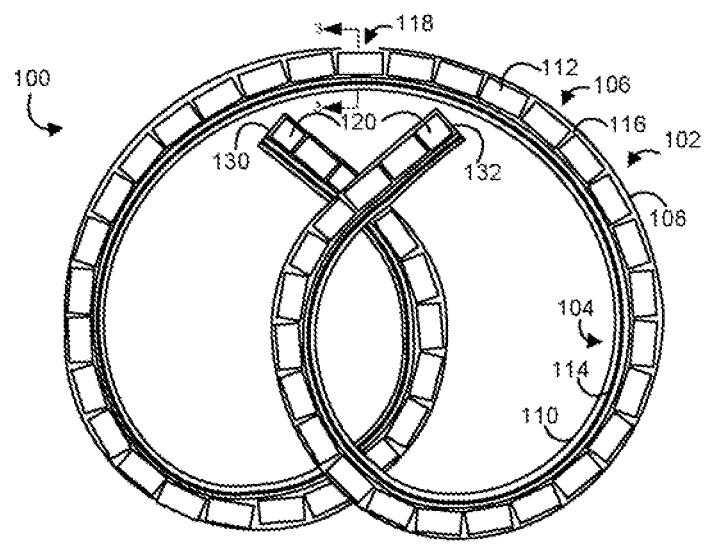
FIG. 11 is a plan view of an embodiment of a drug delivery portion.

An embodiment of a drug delivery portion 100 is illustrated in FIG. 11. The drug delivery portion 100 includes a drug reservoir portion 102 and a retention frame portion 104. In FIG. 11, the drug delivery portion 100 is shown in a relatively expanded shape suited for retention in the body, and in FIG. 12 the drug delivery portion 100 is shown in a relatively lower-profile shape for deployment through the channel 200 of a deployment instrument, such as a cystoscope or other catheter. Following deployment into the body, the drug delivery portion 100 may assume the relatively expanded shape to retain the drug delivery portion in the body cavity or lumen. Although no attaching elements for attaching the drug delivery portion 100 to the ureteral stent portion of the device are illustrated in FIG. 11, it should be appreciated that any attaching element suitable for attaching the drug delivery portion 100 to the ureteral stent portion may be used.

For the purposes of this disclosure, terms such as "relatively expanded shape", "relatively higher-profile shape", or "retention shape" generally denote any shape suited for retaining the drug delivery portion in the intended implantation location, including but not limited to the pretzel shape shown in FIG. 11 that is suited for retaining the device in the bladder. Similarly, terms such as "relatively lower-profile shape" or "deployment shape" generally denote any shape suited for deploying the drug delivery portion into the body, including the linear or elongated shape shown in FIG. 12 that is suited for deploying the device through the working channel of catheter, cystoscope, or other deployment instrument positioned in a lumen of the body, such as the urethra. In embodiments, the drug delivery portion may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery portion 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

In particular, the drug delivery portion 100 includes an elastic or flexible device body 106 that defines a drug reservoir lumen 108 and a retention frame lumen 110. The drug reservoir lumen 108 is designed to house a drug formulation, such as a number of solid drug tablets 112, to form the drug reservoir portion 102. The retention frame lumen 110 is designed to house a retention frame 114 to form the retention frame portion 104. The illustrated lumens 108, 110 are discrete from each other, although other configurations are possible.

Figure 13:
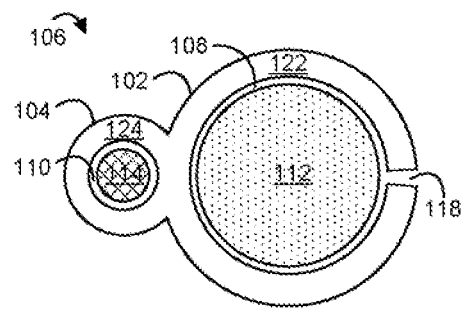
FIG. 13 is a cross-sectional view of the drug delivery portion shown in FIG. 11, taken along line 3-3 in FIG. 11.

As shown in the cross-sectional view of FIG. 13, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed.

An aperture 118 may be formed through the wall 124 that defines the drug reservoir lumen 108. The aperture 118 may provide a passageway for releasing drug from the drug reservoir lumen 108 as further described below. However, the aperture 118 may be omitted in some embodiments.

As shown in FIG. 11, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. However, any number of drug units may be used. The drug reservoir lumen 108 includes an entry 130 and an exit 132, which are shown as relatively circular openings at opposite ends of the drug reservoir lumen 108. The entry 130 provides ingress for the drug units 112 to be placed into the drug reservoir lumen 108 during device loading and assembly, such as by a flow of pressurized gas, in which case the exit 132 provides egress for the flow of pressurized gas to escape from the drug reservoir lumen 108. Once the drug units 112 are loaded, at least two end plugs 120 block the entry 130 and exit 132. The end plugs 120 may be cylindrical plugs inserted into the entry 130 and the exit 132, each having a slightly larger outer diameter than an inner diameter of the drug reservoir lumen 108 so that the plugs substantially enclose the entry 130 and exit 132 and are snugly retained in position. In some cases, a number of end plugs 120 can be positioned in the entry 130 or the exit 132. The end plugs 120 may be silicone plugs. The end plugs 120 also may be omitted, in which case the entry 130 and exit 132 may be closed with a material, such as adhesive, that is placed in the drug reservoir lumen 108 in workable form and cures therein.

In some embodiments, the drug tablets 112 may not fill the entire drug reservoir lumen 108. In such embodiments, a filling material may be used to fill the remainder of the drug reservoir lumen 108. For example, the drug tablets 112 may be loaded in a central portion of the drug reservoir lumen 108 and the filling material may be loaded in the remaining end portions of the drug reservoir lumen 108. The filling material may be inserted into the end portions of the drug reservoir lumen 108 after the lumen is filled with the drug tablets 112. The filling material may be a polymeric material. The polymeric material may be placed in the drug reservoir lumen 108 in workable form and may cure therein. Suitable polymeric materials may cure at room temperature or in response to an external stimulus, such as heat. In some cases, the filling material may enclose the entry 130 and exit 132, in which case the end plugs 120 may or may not be provided. The filling material also may be a number of end plugs 120 inserted into the end portions of the drug reservoir lumen 108.

Once the drug units 112 are loaded, interstices 116 or breaks may be formed between adjacent drug units 112. The interstices or breaks 116 may serve as reliefs that accommodate deformation or movement of the portion 100, while permitting the individual drug units 112 to retain their solid form during storage and deployment. Thus, the drug delivery portion 100 may be relatively flexible or deformable despite being loaded with a solid drug, as each drug unit 112 may be permitted to move with reference to adjacent drug units 112. Along the length of the device drug reservoir lumen 108, the drug units 112 may have the same composition or may vary in composition, and in some cases drug units 112 of different compositions may be in distinct reservoirs that are segregated, either axially or radially, along the length of the drug reservoir lumen 108.

The retention frame lumen 110 is loaded with the retention frame 114, which may be an elastic wire. The retention frame 110 may be configured to spontaneously return to a retention shape, such as the illustrated "pretzel" shape or another coiled shape. In particular, the retention frame 114 may retain the drug delivery portion 100 in the body, such as in the bladder. For example, the retention frame 114 may have an elastic limit and modulus that allows the portion 100 to be introduced into the body in a relatively lower-profile shape, permits the drug delivery portion 100 to return the relatively expanded shape once inside the body, and impedes the device from assuming the relatively lower-profile shape within the body in response to expected forces, such as the hydrodynamic forces associated with contraction of the detrusor muscle and urination. Thus, the drug delivery portion 100 may be retained in the body once implanted, limiting or prevent accidental expulsion.

The material used to form the device body 106 may be elastic or flexible to permit moving the drug delivery portion 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. The flexible material also allows the device body 106 to flex outward or circumferentially expand in response to a flow of pressurized gas through the drug reservoir lumen 108 during drug loading, as described below. The material used to form the device body 106 also may be water permeable or porous so that solubilizing fluid can enter the drug reservoir portion 102 to solubilize the drug units 112 once the device is implanted. For example, silicone or another biocompatible elastomeric material may be used.

In one embodiment in which the drug delivery portion 100 is designed to be implanted in the bladder, the drug delivery portion 100 is designed to be inserted into (and optionally retrieved from) the bladder through the urethra cystoscopically. Thus, the device may be sized and shaped to fit through a narrow tubular path of a deployment instrument, such as a catheter or cystoscope.

A cystoscope for an adult human may have an outer diameter of about 5 to 7 mm and a working channel with an inner diameter of about 2.4 mm to about 2.6 mm. In other embodiments, a cystoscope may have a working channel with a larger inner diameter, such as an inner diameter of 4 mm or more. Thus, the implantable device may be relatively small in size. For example, when the device is elastically deformed to the relatively lower profile shape, the device for an adult patient may have a total outer diameter that is about 3.75 mm or less, such as about 2.6 mm or less. For example, in some embodiments the drug delivery portion may have a total outer diameter from about 3.7 mm to about 2.6 mm. For pediatric patients, the dimensions of the device are anticipated to be smaller, e.g., proportional for example based on the anatomical size differences and/or on the drug dosage differences between the adult and pediatric patients. In addition to permitting insertion, the relatively small size of the device may also reduce patient discomfort and trauma to the bladder.

Figure 14:
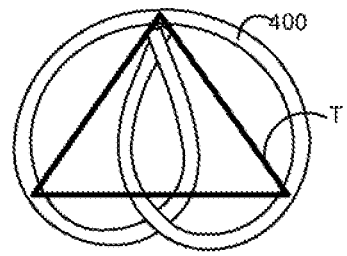
FIG. 14 is an illustration showing the size of an embodiment of a drug delivery portion in comparison to an approximation of the bladder trigone region.

The overall configuration of the drug delivery portion preferably is designed to ensure that the drug delivery portion is tolerable to the patient while it is deployed in vivo. To facilitate tolerability, the size of the drug delivery portion may be smaller than the bladder under most levels of bladder fullness. The size of the human bladder changes depending on whether the bladder is full or empty. The bladder is roughly spherical when full and varies in shape when empty or nearly empty, often assuming a roughly ellipsoidal shape when empty. For the purposes of this disclosure, the diameter of the empty bladder is approximated to be about 3 cm, as the typical empty bladder may have a dimension of about 3 cm in at least one direction. The fullness of the bladder also affects the intravesical pressure therein. Typically, when the bladder contains between about 100 and 200 mL of urine, the pressure within the bladder is between about 8 to 15 cm $H_2O$ (about 0.8 to 1.5 kPa). At these pressures the first sensation of bladder fullness occurs, while lower pressures are mediated by nerves in the bladder wall so that no sensation of bladder fullness is created. As the bladder becomes full, a definite sensation of bladder fullness and an urge to urinate may be created. A full bladder may correspond to intravesical pressures of about 40 and 100 cm $H_2O$ (about 4 kPa to 10 kPa). More particularly, the sensation of an urge to urinate originates within the bladder trigone region, which is an area of the bladder defined between the bladder neck and the ureteral orifices. The trigone can be approximated as a triangle having a top vertex that represents the bladder neck and two bottom vertices that represent the ureteral orifices. FIG. 14 shows an example triangle that approximates the trigone of an adult human male. In a human male, the distance from the bladder neck to one of the ureteral orifices is about 2.75 cm and the distance between the two ureteral orifices is about 3.27 cm. Thus, in FIG. 14, the distance from the top vertex to either of the bottom vertices is about 2.8 cm, while the distance between two bottom vertexes is 3.3 cm. The size of the trigone region may vary depending on the animal. In an adult human female, for example, the distance between the two ureteral orifices is about 2.68 cm and the distance from a neck of the bladder to one of the ureteral orifices is about 2.27 cm. Smaller animals may have smaller trigone regions.

In view of these bladder characteristics, the drug delivery portion may be configured to be tolerable within the bladder. In particular, the drug delivery portion may be sized so that when the device is in the retention shape, the drug delivery portion may be smaller than the bladder under most conditions of bladder fullness. A drug delivery portion that is smaller than the bladder under most conditions of bladder fullness may have reduced contact with the bladder wall, reducing potential irritation of the bladder wall and contact pressure that may be sensed as bladder fullness. However, when the drug delivery portion is in the retention shape, the drug delivery portion may have an overall size and shape that is selected so that when the drug delivery portion overlays the triangular approximation of the bladder trigone region, the drug delivery portion is larger than the triangular approximation. In some embodiments, such sizing may reduce the frequency with which the drug delivery portion rests within the trigone region, which may be sensitive. Such sizing also may limit the likelihood of a portion of the device entering or becoming trapped within the bladder neck and the ureteral orifices.

In some embodiments, the drug delivery portion in a retention shape may have dimensions in all directions that are less than 3 cm, so that when the bladder is empty, contact with the bladder wall may be minimized. In other embodiments, the drug delivery portion in the retention shape may have at least one dimension that is larger than 3 cm, so that a larger drug payload can be delivered. In such embodiments, the bladder wall may exert a pressure on the device that compresses the device in at least one direction so that it fits within the empty bladder, and the compressed device may exert a return pressure on the bladder wall. The return pressure may not exceed those pressures associated with a sensation of urgency of urination or bladder fullness, so that the device remains tolerable. Thus, the size and shape of the drug delivery portion may be selected so that when the device is compressed, the device exerts a pressure on the bladder wall that is less than about 9.8 kPa. In some embodiments, the size and shape of the device may be selected so that when the device is compressed, the device exerts a pressure on the bladder wall that is less than about 3.92 kPa. In particular embodiments, the size and shape of the drug delivery portion may be selected so that when the drug delivery portion is compressed, the drug delivery portion exerts a pressure on the bladder wall that is less than about 1.47 kPa and may be less than 0.79 kPa. These pressure changes can be achieved by varying the overall size of the drug delivery portion and the extent of its surface area. For example, the surface area of the device may be increased to decrease the pressure exerted against the bladder wall upon contact. Thus, the device geometry may be customized to avoid or minimize undesirable contact forces and pressures linked to urgency sensation.

Thus, within the three-dimensional space occupied by the drug delivery portion in the retention shape, the maximum dimension of the device in any direction is less than 10 cm, the approximate diameter of the bladder when filled. In some embodiments, the maximum dimension of the drug delivery portion in any direction may be less than about 9 cm, such as about 8 cm, 7 cm, 6 cm, 5 cm, 4.5 cm, 4 cm, 3.5 cm, 3 cm, 2.5 or smaller. In particular embodiments, the maximum dimension of the drug delivery portion in any direction is less than about 7 cm, such as about 6 cm, 5 cm, 4.5 cm, 4 cm, 3.5 cm, 3 cm, 2.5 cm or smaller. In preferred embodiments, the maximum dimension of the drug delivery portion in any direction is less than about 6 cm, such as about 5 cm, 4.5 cm, 4 cm, 3.5 cm, 3 cm, 2.5 cm or smaller.

More particularly, the three-dimension space occupied by the drug delivery portion is defined by three perpendicular directions. Along one of these directions the drug delivery portion has its maximum dimension, and along the two other directions the drug delivery portion may have smaller dimensions. For example, the smaller dimensions in the two other directions may be less than about 4 cm, such as about 3.5 cm, 3 cm, or less. In a preferred embodiment, the drug delivery portion has a dimension in at least one of these directions that is less than 3 cm.

In some embodiments, the drug delivery portion may have a different dimension in at least two of the three directions, and in some cases in each of the three directions, so that the device is non-uniform in shape. Due to the non-uniform shape, the device may be able to achieve an orientation of reduced compression in the empty bladder, which also is non-uniform in shape. In other words, there may be a particular orientation for the device in the empty bladder that allows the device to exert less contact pressure against the bladder wall, making the device more tolerable for the patient.

The overall shape of the drug delivery portion may enable the drug delivery portion to reorient itself, such as when tethered and separate from the stent portion, within the bladder to reduce its engagement or contact with the bladder wall. For example, the overall exterior shape of the drug delivery portion may be curved, and all or a majority of the exterior or exposed surfaces of the device may be substantially rounded. The drug delivery portion also may be substantially devoid of sharp edges, and its exterior surfaces may be formed from a material that experiences reduced frictional engagement with the bladder wall. Such a configuration may enable the drug delivery portion to reposition itself within the empty bladder so that the device applies lower contact pressures to the bladder wall in some embodiments. In other words, the drug delivery portion may slip or roll against the bladder wall into a lower energy position, meaning a position in which the drug delivery portion experiences less compression.

Figure 12:
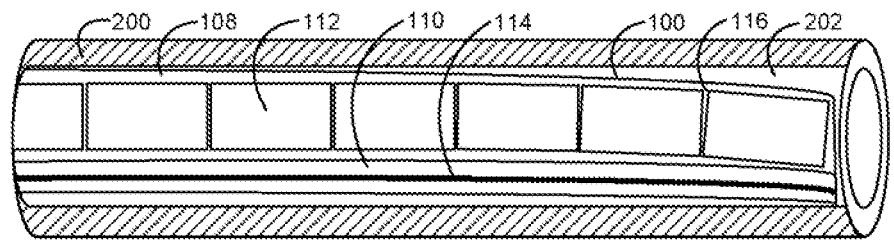
FIG. 12 is a plan view of the drug delivery portion shown in FIG. 11, illustrating the drug delivery portion inside a deployment instrument.

An example of a drug delivery portion that generally satisfies these characteristics is shown in FIGS. 11-13. In particular, the illustrated drug delivery portion is generally planar in shape even though the device occupies three-dimensional space. Such a drug delivery portion may define a minor axis, about which the device is substantially symmetrical, and a major axis that is substantially perpendicular to the minor axis. The drug delivery portion may have a maximum dimension in the direction of the major axis that does not exceed about 6 cm, and in particular embodiments is less than 5 cm, such as about 4.5 cm, about 4 cm, about 3.5 cm, about 3 cm, or smaller. The drug delivery portion may have a maximum dimension in the direction of the minor axis that does not exceed about 4.5 cm, and in particular embodiments is less than 4 cm, such as about 3.5 cm, about 3 cm, or smaller. The drug delivery portion is curved about substantially its entire exterior perimeter in both a major cross-sectional plane and a minor cross-sectional plane. In other words, the overall exterior shape of the drug delivery portion is curved and the cross-sectional shape of the device is rounded. Thus, the drug delivery portion is substantially devoid of edges, except for edges on the two flat ends, which are completely protected within the interior of the drug delivery portion when the drug delivery portion lies in a plane. In some embodiments, these characteristics enable the drug delivery portion to reorient itself into a position of reduced compression when in the empty bladder.

The drug delivery portion also may be small enough in the retention shape to permit intravesical mobility. In particular, in some embodiments, the drug delivery portion when deployed may be small enough to move within the bladder, such as to move freely or unimpeded throughout the entire bladder under most conditions of bladder fullness, facilitating patient tolerance of the device. Free movement of the drug delivery portion may facilitate uniform drug delivery throughout the entire bladder, as opposed to a particular bladder location located near the release orifice. However, drug delivery portions that otherwise move freely within the bladder may be impeded from moving freely when the bladder is completely empty, and yet the drug delivery portion and ureteral stent device may still be tolerable if sufficiently compressible as described above.

In some embodiments, the drug delivery portion also may have a density that is selected to facilitate floatation. In some embodiments, the drug delivery portion has a minimum density in a dry and unloaded state, meaning the device is not loaded with drug and fluid is not present in the device walls or lumens. The density of the drug delivery portion also increases when the device is in a wet state, meaning fluid is present in the device walls and lumens. The drug delivery portion enters the wet state upon implantation in the bladder, as the device becomes surrounded by urine. In use, the drug delivery portion may have a maximum density after implantation, when the drug delivery portion is loaded with the maximum drug payload and liquid displaces any air present in the walls and lumens. Subsequently, the density of the drug delivery portion may remain essentially the same or decrease as the drug is solubilized and released, and replaced by urine.

In general, the drug delivery portion in the dry and loaded state may have a density in the range of about 0.5 g/mL to about 1.5 g/mL, such as between about 0.7 g/mL to about 1.3 g/mL. In some embodiments, the drug delivery portion in the dry and loaded condition has a density that is less than the density of water, such as a density that is less than about 1 g/mL. Such densities facilitate buoyancy and movement in the bladder. Lighter or lower density materials may be integrated into the drug delivery portion as needed to compensate for any higher density drug or other payload in the drug delivery portion, thereby maintaining an overall density that facilitates buoyancy for tolerance purposes. In addition, air or another gas may be trapped in portions of the drug delivery portion to reduce the overall density. For example, the walls of retention frame lumen may be made impermeable to water such that an air pocket is formed in the retention frame lumen about the elastic wire.

One example drug delivery portion may have a mass of about 0.40 grams or less and a density of about 0.7 g/mL or less when unloaded. The drug delivery portion may be loaded with a drug having a mass of about 275 mg or less. In such embodiments, the drug delivery portion when loaded may have a mass of about 0.675 grams or less and a density of about 1.1 g/mL or less. Such a device may be well tolerated in the bladder. Drug delivery portions of smaller masses and densities may likewise be well tolerated.

The exact configuration and shape of the drug delivery portion may be selected depending upon a variety of factors including the overall device design and how the drug delivery portion is connected to the stent portion, the deployment means, drug, dosage regimen, and treatment needs of the patient. For example, the design of the device may minimize the patient's pain and discomfort, while locally delivering a therapeutically effective dose of the drug to a tissue site (e.g., urothelial tissue) in a patient.

In one embodiment, the implantable drug delivery portion can be made to be completely or partially bioerodible so that no explanation, or retrieval, of the drug delivery portion is required following release of the drug formulation. As used herein, the term "bioerodible" means that the device, or part thereof, degrades in-vivo by dissolution, enzymatic hydrolysis, erosion, resorption, or a combination thereof. In one embodiment, this degradation occurs at a time that does not interfere with the intended kinetics of release of the drug from the drug delivery portion. For example, substantial erosion of the drug delivery portion may not occur until after the drug formulation is substantially or completely released. In another embodiment, the drug delivery portion is bioerodible and the release of the drug formulation is controlled at least in part by the degradation or erosion characteristics of the erodible device body.

Alternatively, the implantable drug delivery portion may be at least partially non-bioerodible. In some embodiments, the drug delivery portion is formed from materials suited for urological applications, such as medical grade silicone, natural latex, PTFE, ePTFE, PLGA, PGS, stainless steel, nitinol, elgiloy (non ferro magnetic metal alloy), polypropylene, polyethylene, polycarbonate, polyester, nylon, or combinations thereof. Following release of the drug formulation, the ureteral stent device, drug delivery portion and/or the retention frame may be removed substantially intact or in multiple pieces. In some embodiments, the drug delivery portion is partially bioerodible so that the drug delivery portion, upon partial erosion, breaks into non-bioerodible pieces small enough to be excreted from the bladder. Useful biocompatible bioerodible and non-bioerodible materials of construction are known in the art.

In a preferred embodiment, the ureteral stent device and drug delivery portion is sterilized, such as after the device is manufactured/assembled and before the device is implanted. In some cases, the ureteral stent device and drug delivery portion may be sterilized after the device is packaged, such as by subjecting the package to gamma irradiation or ethylene oxide gas.

(i) The Drug Reservoir Portion

In one embodiment, the drug reservoir portion of the device includes an elongated tube. An interior of the tube may define one or more drug reservoirs, and a drug formulation may be housed in the drug reservoir(s). In another embodiment, the drug reservoir portion is in a form other than a tube.

The release rate of the drug from the drug reservoir portion generally is controlled by the design of the combination of the device components, including but not limited to the materials, dimensions, surface area, and apertures of the drug reservoir portion, as well as the particular drug formulation and total mass of drug load, among others.

An example of such a drug reservoir portion is shown in FIGS. 11-13. As shown, the drug reservoir portion 102 may include a body formed from an elastomeric tube 122. The tube 122 defines a reservoir 108 that contains a number of drug tablets 112. Ends of the tube 122 may be sealed with sealing structures 120. At least one aperture 118 may be disposed in the tube 122. In cases in which an aperture 118 is provided, the aperture 118 may be closed by a degradable timing membrane, which may control the initiation of release of the drug formulation from the reservoir. In some cases, a sheath or coating may be positioned about at least a portion of the tube 122 to control or reduce the release rate, such as by reducing the osmotic surface area of the tube or by reducing diffusion through the tube wall. For simplicity, the degradable timing membranes and sheaths or coatings are not shown.

In one embodiment, the drug reservoir portion operates as an osmotic pump. In such embodiments, the tube may be formed from a water permeable material, such as a silicone, or tube may have a porous structure, or both. Following implantation, water or urine permeates through the wall of the tube, one or more apertures formed through the tube, or one or more passing pores formed through a porous tube. The water enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles, which are described, for example, in Theeuwes, *J. Pharm. Sci.*, 64(12): 1987-91 (1975). In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Application Publication No. 2009/0149833.

In an alternative embodiment, the device may operate essentially by diffusion of the drug from the tube through (i) one or more discrete apertures formed in the wall of the tube, or passing pores formed in the wall of a porous tube, or (ii) through the wall of the tube itself, which may be permeable to the drug, or (iii) a combination thereof. In embodiments in which diffusion occurs through the wall, the apertures or passing pores may not be included. In still other embodiments, the device may operate by a combination of osmosis and diffusion.

The drug reservoir portion may be formed from an elastomeric material, which may permit elastically deforming the device during its deployment through a deployment instrument such as a cystoscope or catheter. For example, the tube may be elastically deformed along with the retention frame for intravesical implantation, as described in further detail below.

In preferred embodiments, the drug reservoir portion is formed from a material that is both elastomeric and water permeable. One material that is both elastomeric and water permeable is silicone, although other biocompatible materials may be used.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof.

In some embodiments, the device body is bioerodible. In one embodiment of a bioerodible device, the tube of the body is formed of a biodegradable or bioresorbable polymer.

Examples of suitable such materials include synthetic polymers selected from poly(amides), poly(esters), poly(ester amides), poly(anhydrides), poly(orthoesters), polyphosphazenes, pseudo poly(amino acids), poly(glycerol-sebacate) (PGS), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis(s-caprolacton-4-yl)propane to obtain elastomeric properties.

The tube of a drug reservoir portion tube may be substantially linear and in some cases may be substantially cylindrical with a circular cross-section, although square, triangle, hexagon, and other polygonal cross-sectional shapes can be used, among others.

The ends of the tube may be sealed to limit escape of the drug, such as with a sealing structure or other sealing means. The sealing structure may have any shape suited to plug or close the tube end, such as a cylinder 120 as shown in FIG. 11, a ball, a disk, or others. In some embodiments, the sealing structure may have a larger diameter than the inner diameter of the tube, such that the tube stretches to fit tightly about the sealing structure, closing the tube and retaining the sealing structure in place. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the tube may have multiple reservoirs. Each reservoir may be defined by a portion of the tube inner surface and at least one partition. The partition may be a partition structure or plug inserted into the tube, such as a cylinder, sphere, or disk, among others, in which case the partition structure may have a larger cross-section than the tube, securing the partition structure in place and segregating adjacent reservoirs. For example, the cylindrical plug 120 of FIG. 11 that closes the tube end may instead serve as a partition structure to segregate two reservoirs positioned adjacent to each other along the length of the tube. The partition may be non-porous or semi-porous, non-resorbable or resorbable and may be formed of a material described above with reference to the cylindrical plug 120. The partition also may be formed in the tube, such as by molding. For example, one or more webs may extend through the tube along its length to segregate axial reservoirs that extend along the length of the tube, as shown in Examples J through L of FIG. 16. The partition also may be a structure that joins two different tubes that serve as separate reservoirs, as shown in Examples M through O of FIG. 16.

The multiple reservoirs permit segregating two or more different drug formulations in different reservoirs, delivering a single drug from different reservoirs at different rates or times following implantation, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

For example, the onset of release of two doses in different reservoirs can be staged by configuring the device accordingly, such as by using different materials for portions of the tube defining different reservoirs, by associating the aperture(s) of different reservoirs with different timing membranes, by placing drugs with different solubilities in the reservoirs, or by placing drugs with different forms in the reservoirs, such as a liquid form for immediate release and a solid form to be solubilized prior to release. Thus, the device may release some drug relatively quickly after implantation while other drug may experience an induction time before beginning release.

In one embodiment, the total volume of the reservoir (or combined reservoirs) is sufficient to contain all the drug needed for local delivery over the course of a single treatment, reducing the number of procedures needed to treat a particular condition.

(ii) Drug Release Apertures

In some embodiments, the device includes one or more apertures or orifices for dispensing the drug, such as via osmosis, diffusion, or a combination thereof, among other. The apertures may be spaced along the tube to provide a passageway for release of the drug formulation. The apertures or orifices may be positioned through a sidewall or an end of the tube. The apertures may be in fluid communication with one or more reservoirs. Embodiments of apertures 118 are shown on the drug reservoir portions in FIGS. 11 and 13, respectively.

The aperture may be located about a middle of the drug reservoir portion or adjacent to its exit, which may affect the ease of loading solid drug units into the drug reservoir portion as described below. The apertures may be positioned away from a portion of the tube that will be folded during insertion to limit tearing of degradable membranes on the apertures.

In embodiments in which the drug deliver portion includes a device body that defines both drug reservoir and retention frame lumens, such as the embodiment shown in FIG. 13, the aperture or apertures may have various positions on the wall of the drug reservoir lumen with reference to the wall of the retention frame lumen, as further described below.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 μm and about 800 μm, such as between about 25 μm and about 500 μm, and more particularly between about 30 μm and about 400 μm. In one example, the aperture has a diameter between about 100 μm and about 300 μm, such as about 150 μm. The length of the aperture has also been observed to affect whether the release is in the osmotic regime, e.g., a 5 mm length and 500 μm diameter aperture may provide osmotic release. In embodiments where the device operates primarily by diffusion, the apertures may be in this range or larger. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube. The aperture also may be formed in an orifice structure disposed in an end of the tube, such as a ruby or sapphire precision orifice structure from, for example, Bird Precision Orifices, Swiss Jewel Company.

In some embodiments, the drug reservoir portion may not have any apertures, in which case the drug may be released via a release mechanism other than osmosis, such as diffusion through the wall of the drug reservoir portion. Similarly, a drug reservoir portion having multiple discrete drug reservoirs may have apertures associated with all, some, or none of the drug reservoirs, in which cases release from the different drug reservoirs may occur via different release mechanisms.

In one embodiment, a degradable membrane, i.e., a timing membrane, is disposed over or in the apertures (e.g., in register with the aperture) to control the onset of release of the drug formulation. The degradable membrane may be a coating over all or some of the outer surface of the tube or a discrete membrane above or within the aperture. Two or more degradable membranes also may be used to control release from one aperture. The membranes may be formed, for example, of a resorbable synthetic polymer (such as polyester, a poly(anhydride), or a polycaprolactone) or a resorbable biological material (such as cholesterol, other lipids and fats). Additional details are described in U.S. Application Publication No. 2009/0149833.

(iii) Drug Formulation and Solid Drug Tablets

The drug formulation can include essentially any therapeutic, prophylactic, or diagnostic agent, such as one that would be useful to deliver locally to a body cavity or lumen or regionally about the body cavity or lumen. The drug formulation may consist only of the drug, or one or more pharmaceutically acceptable excipients may be included. The drug may be a biologic. The drug may be a metabolite. As used herein, the term "drug" with reference to any specific drug described herein includes its alternative forms, such as salt forms, free acid forms, free base forms, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation desirably includes no or a minimum quantity of excipient for the same reasons of volume/size minimization.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. For example, lidocaine base may be released via diffusion through a silicone wall without an aperture, and the release rate may be increased by adding apertures to the wall. Thus, the drug may be formulated to have a high or low solubility depending on the intended release mode. In one embodiment, the drug is formulated to improve its apparent solubility in the implantation environment, such as its apparent solubility in urine within the bladder.

In a particular embodiment, the drug release portion of the devices described herein provides pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meptylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocalne, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, naproxen.

In certain embodiments, the drug delivery portion is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin. Evidence suggests that the bladder expresses nerve growth factor (NGF) locally, since exogenously delivered NGF into the bladder induces bladder hyperactivity and increases the excitability of dissociated bladder afferent neurons (*Nature Rev Neurosci* 2008; 9:453-66). Accordingly, it would be advantageous to locally deliver a MAB or other agent against NGF using the described delivery devices, significantly reducing the total dose needed for therapeutic efficacy. Evidence also suggests that binding of the alpha-2-delta unit of voltage-sensitive calcium channels, such as with gabapentin, may be effective in the treatment of diseases of neuropathic pain such as fibromyalgia and that there may be common mechanisms between IC and diseases of neuropathic pain (See *Tech Urol*. 2001 Mar. 7(1):47-49). Accordingly, it would be advantageous to locally deliver a calcium channel alpha-2-delta modulator, such as PD-299685 or gabepentin, using the described delivery devices, minimizing does-related systemic toxicities in the treatment of IC.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In one particular embodiment, the drug delivery portion is used in association with the placement of a ureteral stent, such as to treat pain, urinary urgency or urinary frequency resulting from ureteral stent placement. Non-limiting examples of specific drugs for such treatment include antimuscarinics, α-blockers, narcotics, and phenazopyridine, among others.

The drug delivery portion can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In another embodiment, the drug delivery portion is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an antileukin, or the like. The drug may be an immunomodulator, such as a TLR agonist, including imiquimod or another TLR7 agonist. The drug may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough).

In still another embodiment, the present intravesical drug delivery portion is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, gentamicin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery portion is used to treat fibrosis. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The implantable drug delivery portion also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including GABAB agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

The possible drug useful for treatment of neurogenic bladder may be categorized into one of two general types: those for treating spastic neurogenic bladder and those for treating flaccid neurogenic bladder. In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

In some embodiments, the drug formulation is in solid form. For example, the drug formulation is formed into solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation). The drug units may be in the form of tablets, pellets, or beads, although other configurations are possible. For example, FIGS. 11-13 illustrate a number of the solid drug units 112 loaded into the drug reservoir lumen 108 of the drug delivery portion 100, the drug units 112 being suited for implantation.

The drug tablets may be made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in-vivo dissolution and drug release characteristics. The drug formulation also may be loaded into the drug reservoir in workable form and may cure therein. Thereafter, the solidified drug may be broken along the length of the drug reservoir to form the interstices or breaks that permit device deformation. For example, in embodiments in which the drug formulation is configured to be melted and solidified, the drug formulation can be melted, injected into the drug reservoir in melted form, solidified in the drug reservoir, and broken into pieces in the drug reservoir to accommodate device deformation or movement. The drug formulation also may be extruded with the drug reservoir, may cure within the drug reservoir, and subsequently may be broken along the length of the reservoir to accommodate device deformation.

The drug tablet may include a drug component and may include an excipient component. The drug component may include one or more drugs or active pharmaceutical ingredients (API), while the excipient component may include one or more excipients. The term "excipient" is known in the art, and representative examples of excipients useful in the present drug tablets may include ingredients such as binders, lubricants, glidants, disintegrants, colors, fillers or diluents, coatings and preservatives, as well as other ingredients to facilitate manufacturing, storing, or administering the drug tablet.

In order to maximize the amount of drug that can be stored in and released from a given drug delivery portion of a selected (small) size, the drug tablet preferably comprises a high weight fraction of drug or API, with a reduced or low weight fraction of excipients as are required for tablet manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug tablet is more than 50% by weight drug. In a preferred embodiment, 75% or more of the weight of the drug tablet is drug, with the remainder of the weight comprising excipients, such as lubricants and binders that facilitate making the drug tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug tablet. In some cases, the drug content comprises about 75% or more of the weight of the drug tablet. More particularly, the drug content may comprise about 80% or more of the weight of the drug tablet. For example, the drug content may comprise between about 85% and about 99.9% of the weight of the drug tablet. In some embodiments, the excipient content can be omitted completely.

In one embodiment, the drug and excipients are selected and the tablet formulated to be water soluble, so that the drug tablets can be solubilized when the device is located within the vesical, to release the solubilized drug. In a preferred embodiment, the drug tablets are formulated to be sterilizable, either within or outside of the drug delivery portion, without substantial or detrimental changes in the chemical or physical composition of the drug tablets. Such drug tablets may be quite different from conventional drug tablets, which typically include active ingredients that constitute less than 50% of the drug tablet content by weight, with the remainder of the drug tablet comprising excipients that are often insoluble and/or may not be suited for conventional sterilization. Furthermore, the present drug tablets may be sized and shaped for use with an implantable drug delivery portion. For example, the drug tablets may be "mini-tablets" that are much smaller in size than conventional tablets, which may permit inserting the drug tablets through a lumen such as the urethra into a cavity such as the bladder. An embodiment of a solid drug tablet 112 for intravesical insertion or other in vivo implantation is shown in FIGS. 11-13. In a preferred embodiment, the drug tablets are mini-tablets which comprise greater than 80% lidocaine hydrochloride monohydrate.

In embodiments in which one or more pharmaceutically acceptable excipients are included, the excipients may facilitate loading the solid drug units in the device. For example, the excipients may increase the lubricity of the drug units so that the drug units can slide with reference to the interior lumen walls of the drug reservoir portion. The excipients also may facilitate forming the therapeutic agent or agents into a solid drug tablet that can be loaded into the drug reservoir portion. The excipients also may affect the kinetics of drug release from the device, such as by increasing or retarding the solubility or dissolution rate of the drug units. In some embodiments, however, the drug release rate is predominately controlled by characteristics of the drug reservoir, such as the tube thickness and permeability to water or urine, while the excipient content of the drug units is primarily selected to permit reliable production of drug units that are solid and include a relatively high weight fraction of drug.

Although mini-tablets and other solid drug tablets are described herein as having a high weight fraction of drug or API and a low weight fraction of excipients, the solid drug tablets may have any weight fraction of drug, especially in cases in which the tablet includes a drug that is extremely potent, a stabilizing agent, or an agent that increases the solubility of the drug, among others or combinations thereof.

The individual drug units may have essentially any selected shape and dimension that fits within the drug reservoir portion of the device. In one embodiment, the drug units are sized and shaped such that the drug reservoir portion is substantially filled by a select number of drug units. Each drug unit may have a cross-sectional shape that substantially corresponds to a cross-sectional shape of the drug reservoir portion. For example, the drug units 112 are substantially cylindrical in shape as shown in FIGS. 11-13 for positioning in the substantially cylindrical drug reservoir lumen 108 shown in FIG. 11. Once loaded, the drug units 112 may substantially fill the drug reservoir lumen 108, forming the drug reservoir portion 102.

The drug units may have outer dimensions that are about the same as, are slightly less than, or slightly exceed inner dimensions of the elastic drug reservoir portion. Using larger diameter drug units may increase the payload and thus the amount of drug that can be delivered from a drug delivery portion of a given size. For example, the drug unit 112 shown in FIGS. 11-13 has an outer diameter that slightly exceeds an inner diameter of the drug reservoir lumen 108 shown in FIG. 13. Such drug units 112 may be loaded into the lumen 108 under a flow of pressurized gas that radially expands the drug reservoir wall 122 so that the drug units 112 may travel through the drug reservoir lumen 108 in an axial direction, and when the flow of pressurized gas is removed, the wall 122 may return to retain the drug units 112 in selected axial positions along the length of the lumen 108, as shown in FIG. 11. In embodiments in which the outer dimensions of the drug units are smaller than the inner dimensions of the drug reservoir portion, the drug units may have reduced contact with the drug reservoir portion.

In particular embodiments, the drug units are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery portion may be relatively flexible or deformable despite being loaded with a solid drug, as each drug unit may be permitted to move with reference to adjacent drug units.

An example is shown in FIGS. 11-13, which illustrates the drug unit 112 having circular flat end faces and a cylindrical side wall. Thus, the drug unit 112 can be aligned in a row with other drug units 112 for loading into the cylindrical drug reservoir lumen 108 as shown in FIGS. 11 and 12. When so loaded, the drug units 112 substantially fill the drug reservoir lumen 108, with interstices or breaks 116 formed between them to accommodate deformation or movement. The flat end faces permit piecewise flexibility of the device while limiting the volume or space within the drug reservoir portion that is devoted to the interstices or breaks 116. Thus, the device can be substantially filled with solid drug while retaining its flexibility. Loading the device with a number of drug tablets 112, such as drug tablets that are relatively uniform in size and shape, beneficially permits manufacturing a device that behaves as expected in response to expected forces during and after implantation and exhibits expected drug release characteristics once implanted; that is, the tablet uniformity advantageously enables reproducibility in producing the medical product and thereby generally provides reliable, repeatable drug release characteristics.

In some embodiments, the drug units are relatively tall with respect to their diameter, unlike conventional drug tablets that tend to be short with respect to their diameter. The drug units may be tall enough to retain their orientation once loaded in the drug reservoir, with reduce tipping or rolling. On the other hand, the drug units may be short enough to provide enough interstices or breaks so that the device can flex or move along its length. In particular, each drug unit may have a length that exceeds its width, meaning an aspect ratio of height:width that is greater than 1:1. Suitable aspect ratios for the drug units may be in the range of about 3:2 to about 5:2, although other aspect ratios are possible, including aspect ratios that are less than 1:1, like conventional drug tablets. An example is shown in FIG. 11, which illustrates the drug unit 112 with a length that exceeds its diameter.

In embodiments in which the solid drug tablets are designed for insertion or implantation in a lumen or cavity in the body, such as the bladder, via a drug delivery portion, such as a device of the type described above with reference to FIGS. 11-13, the drug tablets may be "mini-tablets" that are suitably sized and shaped for insertion through a natural lumen of the body, such as the urethra. For the purpose of this disclosure, the term "mini-tablet" generally indicates a solid drug tablet that is substantially cylindrical in shape, having end faces that are relatively planar or flat and a side face that is substantially cylindrical. An example mini-tablet is shown in FIG. 11. The mini-tablet 112 has a diameter, extending along the end face, in the range of about 1.0 to about 3.2 mm, such as between about 1.5 and about 3.1 mm. The mini-tablet 112 has a length, extending along the side face, in the range of about 1.7 mm to about 4.8 mm, such as between about 2.0 mm and about 4.5 mm. The friability of the tablet may be less than about 2%. Embodiments of solid drug tablets and systems and methods of making the same are further described with reference to U.S. Patent Applications incorporated by reference herein.

In a preferred embodiment, the drug tablets include lidocaine. A drug delivery portion having drug tablets that primarily comprise lidocaine may be wholly deployed in the bladder of a patient in need of treatment for interstitial cystitis, neurogenic bladder, or pain, among others. Other diseases or conditions may also be treated using this device. In other embodiments, other drugs, alone or in combination with lidocaine, may be used to treat interstitial cystitis or other diseases and conditions involving the bladder.

Once the solid drug tablets are formed, the drug tablets may be loaded into the drug delivery portion. After the device is loaded, the device preferably is sterilized. The selected sterilization process does not undesirably alter the physical or chemical composition of the solid drug tablets or other components of the device. Examples of suitable sterilization processes include gamma irradiation or ethylene oxide sterilization, although other sterilization processes may be used. For example, gamma irradiation at a strength of about 8 KGy to about 40 KGy, such as about 25 KGy, can be employed. The drug tablets can be sterilized before or after loading/assembly into a drug delivery portion, and the drug tablets possess a commercially reasonable shelf life.

Once implanted, the composition of the drug tablets is appropriate for the intended route of administration, is stable in acidic conditions, and provides pre-selected, reproducible drug release kinetics. For example, the drug tablets may be solubilized in the bladder to continuously release drug at a suitably stable rate drug over an extended period.

(iv) Retention Frame Portion

The drug delivery portion may include a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent premature expulsion of the device from the body under expected forces. For example, the device may be retained in the bladder during urination or contraction of the detrusor muscle.

In a preferred embodiment, the retention frame includes or consists of an elastic wire. In one embodiment, the elastic wire may comprise a biocompatible shape-memory material or a biodegradable shape memory polymer known in the art. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

For example, in the embodiment shown in FIGS. 11-12, the retention frame 114 is an elastic wire formed from a superelastic alloy, such as nitinol, and surrounded by the wall 124 of the retention frame lumen 310, which forms a protective sheath about the retention frame 114. Thus, the wall 124 may be formed from a polymer material, such as silicone. In other embodiments, the retention frame may be an elastic wire formed from a superelastic alloy, such as nitinol, that is covered in a polymer coating, such as a silicone sheath and is attached to the drug reservoir portion.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shapes shown in FIG. 11, the device may occupy a space having dimensions suited to impede expulsion from the bladder. When the retention frame is in the relatively lower-profile shape, such as the elongated shapes shown in FIG. 12, the device may occupy an area suited for insertion into the body, such as through the working channel of a deployment instrument. The properties of the elastic wire cause the device to function as a spring, deforming in response to a compressive load but spontaneously returning to its initial shape once the load is removed. The polymer coating may make the outer surface of the retention frame relatively smooth and soft, reducing irritation of the bladder or other implantation site.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

Figure 15:
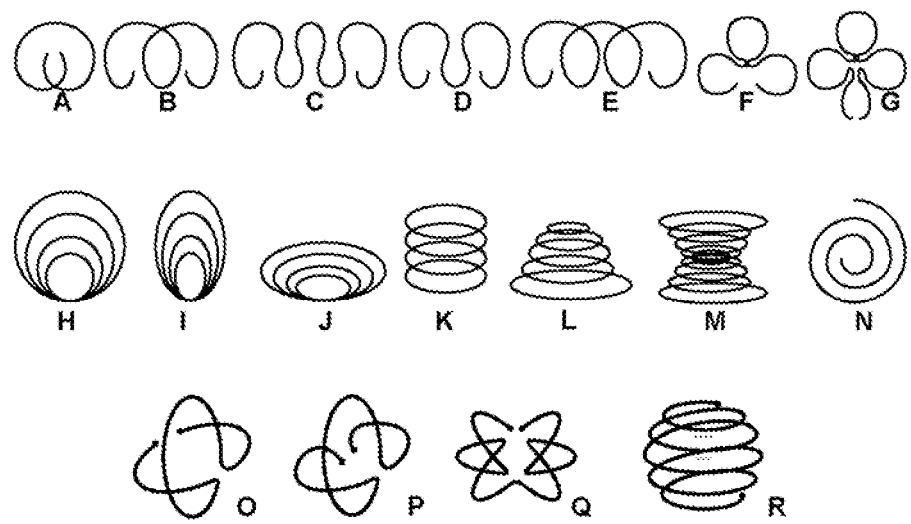
FIG. 15 illustrates examples of shapes for a retention frame of a drug delivery portion.

Examples are shown in FIG. 15. The retention frame may have a two-dimensional structure that is confined to a plane, a three-dimensional structure, such as a structure that occupies the interior of a spheroid, or some combination thereof. In particular, Examples A through G illustrate frames comprising one or more loops, curls, or sub-circles, connected either linearly or radially, turning in the same or in alternating directions, and overlapping or not overlapping. Examples H through N illustrate frames comprising one or more circles or ovals arranged in a two-dimensional or a three-dimensional configuration, the circles or ovals either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Examples O through R illustrate retention frame portions that are shaped to occupy or wind about a spherical space, with each retention frame portion shown above a representation of the frame in a sphere. The retention frame portion may generally take the shape of two intersecting circles lying in different planes as shown in Example O, two intersecting circles lying in different planes with inwardly curled ends as shown in Example P, three intersecting circles lying in different planes as shown in Example Q, or a spherical spiral as shown in Example R. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention housing may be omitted, in which case the retention portion may be components of the drug portion itself, which may assume or may be deformed into a retention shape, or the retention portion may be an anchor associated with the drug portion. Examples of alternative configurations are described in the U.S. patent applications incorporated by reference herein.

(v) Other Drug Delivery Portion Features

The drug reservoir portion can include a coating or a sheath, which may be substantially impermeable to water or relatively less permeable to water than the drug reservoir portion to reduce or alter the osmotic or diffusive surface area of the device body. Thus, the release rate can be independently controlled or targeted with reduced adjustment of desired device characteristics, such as size, shape, material, permeability, volume, drug payload, flexibility, and spring constant, among others. To achieve the release rate, the coating or sheath may cover all or any portion of the device body, and the coating or sheath may be relatively uniform or may vary in thickness, size, shape, position, location, orientation, and materials, among others and combinations thereof. Further, multiple coatings or sheaths may be provided along different portions of the device body, about the same drug reservoir or different drug reservoirs housing the same or different drug formulations. In cases in which the drug reservoir portion is formed from silicone tubing, for example, a coating may be formed from parylene, while a sheath may be formed from a polymer such as polyurethane or curable silicone, or another biocompatible coating or sheath material known in the art. In some embodiments, the coating or sheath may be positioned on the tube between the end and the orifice so that water permeating through the tube adjacent to the end can drive through the portion of the tube covered by the sheath and out of the orifice, reducing or avoiding isolation or stagnation of the drug under the sheath. Coatings and sheaths, and equations for selecting such designs, are described in U.S. Patent Publication No. 2009/0149833.

In one embodiment, the drug delivery portion includes at least one radio-opaque portion or structure to facilitate detection or viewing (e.g., by X-ray imaging or fluoroscopy) of the device by a medical practitioner as part of the deployment or retrieval procedure on a patient. In one embodiment, the tube is constructed of a material that includes a radio-opaque filler material, such as barium sulfate or another radio-opaque material known in the art. Some tubing may be made radio-opaque by blending radio-opaque fillers, such as barium sulfate or another suitable material, during the processing of the tubing. The radio-opaque material also may be associated with the retention frame. For example, a platinum wire may be wound about ends of the elastic wire and covered in smoothening material. Ultrasound imaging may be used. Fluoroscopy may be the preferred method during deployment/retrieval of the non-erodible device by providing accurate real-time imaging of the position and orientation of the device to the practitioner performing the procedure.

In one embodiment, the body of the implantable drug delivery portion further includes at least one retrieval feature, such as a string, loop or other structure that facilitates removal of the device from the body cavity, for example for removal of a non-resorbable device body following release of the drug formulation. The drug delivery portion may be retrieved simultaneously with the ureteral stent portion. In these and in other embodiments, the device may be retrieved using conventional endoscopic grasping instruments, such as forceps or other grasping instruments.

(vi) Combination of the Drug Reservoir Portion and Retention Portion

The drug reservoir portion and the retention frame portion are associated with each other to form the drug delivery portion. A variety of different associations are envisioned.

Figure 16:
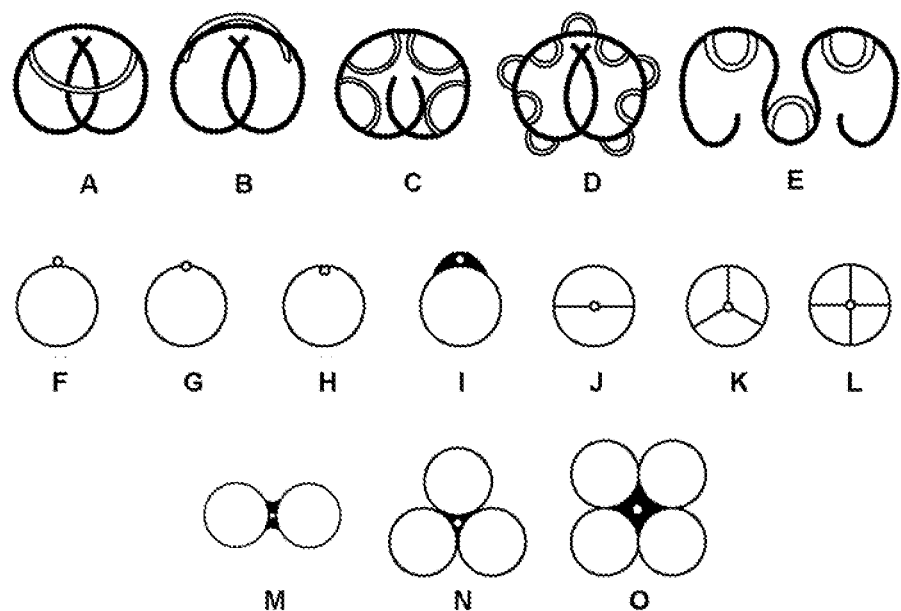
FIG. 16 illustrates examples of configurations for drug delivery portions having at least one drug reservoir portion and a retention frame portion.

For example, the drug reservoir portion and the retention frame portion may be at least partially aligned. In other words, the drug reservoir portion may extend along a portion or the entire length of the retention frame portion, substantially parallel or coincident with the retention frame portion. An example of such an embodiment is shown in FIGS. 11-13. FIG. 16 also illustrates several alternative embodiments in cross-section. As shown in Examples F, G, H, and I, the retention frame wire may extend along either an exterior surface of the drug reservoir wall, along an interior surface of the drug reservoir wall, through the drug reservoir wall, or within a reinforced area inside or outside of the wall. As shown in Examples J, K, and L, the elastic wire may also be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs that may be suited for holding different drug formulations. The web may be formed from the same material as the tube, or from a material having a different permeability to water or urine, depending on the embodiment. As shown in Examples M, N, and O, the elastic wire may be associated with multiple tubes, extending along or between the tubes. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion may be attached to only portion of the retention frame. The drug reservoir portion may have first and second end portions that are attached to a portion of the retention frame. The end portions of the drug reservoir may terminate at the retention frame, the end portions may overlap the retention frame, or a combination thereof. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion. Examples A through E of FIG. 16 illustrate such embodiments.

In other embodiments, the drug reservoir portion and the retention frame portion may be the same component in some embodiments. In such cases, the device may comprise a tube formed in a configuration having a sufficient spring constant to retain the device in the body, as described above. Also, the drug reservoir portion may be wrapped around the retention frame portion, one or any number of times.

The embodiments described herein may be combined and varied to produce other drug delivery portions that fall within the scope of the present disclosure. For example, the drug reservoir portion may be attached to any portion of the retention frame portion in any manner. Multiple drug reservoir portions may be provided, a single drug reservoir portion may be partitioned, or a combination thereof, which may facilitate delivering multiple different drugs into the body, delivering different forms of drugs into the body, delivering drugs at varying rates into the body, or a combination thereof.

Furthermore, when the device is in the retention shape, the retention frame portion may have any orientation with reference to the drug reservoir portion, lying either inside, outside, above, or below the drug reservoir portion or moving with reference to the drug reservoir portion as the device moves through the implantation site. For example, in one embodiment, the drug delivery portion 100 includes a retention frame portion that lies inside the perimeter of the drug reservoir portion. In other embodiments, the drug delivery portion includes a retention frame portion that lies below the drug reservoir portion (such that the retention frame portion would not be visible in FIG. 11). A particular orientation between the two portions can be maintained by filling the retention frame portion with a filling material, such as a silicone adhesive, after the retention frame is loaded. The filling material may cure or solidify to prevent movement of one portion with reference to the other. Other means of maintaining the orientation of the retention frame portion with reference to the drug reservoir portion also can be used.

It should be noted that the device 400 shown in FIG. 14 has a slightly different shape and configuration than the drug delivery portion 100 shown in FIG. 11. For example, the ends of the device 400 are relatively straighter than the ends of the drug delivery portion 100. The straighter ends may result because the retention frame of the device 400 has relatively straight end portions, while the retention frame of the drug delivery portion 100 has relatively curved end portions. A retention frame with relatively straight end portions may be less likely to puncture the walls of the device body during drug loading and thereafter, reducing the risk of device failure after implantation. However, either retention frame shape can be used.

In the embodiment shown in FIG. 11, for example, the drug delivery portion 100 is suited for delivering a drug into the bladder. The drug reservoir lumen 108 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 108 may hold about 10 to 100 cylindrical drug tablets, such mini-tablets. The mini-tablets may each having a diameter of about 1 to about 3. mm, such as about 1.5 mm, and a length of about 1 to about 5 mm, such as about 2 to about 4.5 mm. Such mini-tablets may have a lidocaine payload of about 3.0 to about 40.0 mg. One particular example of a mini-tablet may have a diameter of about 1.5 mm, a length of about 2.1 mm, and a mass of about 4 to 4.5 mg lidocaine. Another particular example of a mini-tablet may have a diameter of about 2 mm, a length of about 3 mm, and a mass of about 12 to 13 mg lidocaine. Yet another particular example of a mini-tablet may have a diameter of about 2.6 mm, a length of about 3.5 to 3.9 mm, and a mass of about 21 to 24 mg lidocaine. Still another particular example of a mini-tablet may have a diameter of about 3 mm, a length of about 4 mm, and a mass of about 33 to 37 mg lidocaine. However, other diameters, lengths, and masses can be used.

Within these ranges, the device may be designed to deliver between about 150 mg and 1000 mg of lidocaine to the bladder, such as about 200 mg, about 400 mg, about 600 mg, or about 800 mg of lidocaine. For example, a smaller payload may be delivered from a smaller device or from a device loaded with fewer tablets, the remainder of the space in the device being loaded with a spacer or filling material.

The foregoing specific configurations are merely possibilities of the type of drug delivery portions that may be created by a person skilled in the art upon reading the present disclosure. For example, in some embodiments the drug reservoir portion may be omitted completely, and the retention frame portion may be associated with another component for retention in the body, such as the bladder. Examples of other components include diagnostic equipment, test materials, and small electronic devices, such as cameras and sensors, among others.

Methods of Using the Ureteral Stent Device

Methods of delivering drug from a ureteral stent device are also disclosed herein. One method includes (i) implanting a ureteral stent device in a ureter of a patient, the ureteral stent device including a drug delivery component; and (ii) releasing a drug from the drug delivery component into the patient's body at or about the site of implantation.

Methods also are provided for preventing or treating one or more side effects associated with placement of the ureteral stent in the body, such as bladder pain, discomfort, urinary urgency, or urinary frequency. One such method includes (i) implanting a ureteral stent device in a ureter of a patient; and (ii) releasing a drug from the ureteral stent device into the patient, the drug selected from the group consisting of: a local anesthetic agent, an anti-muscarinic, an alpha-blocker, a narcotic, and phenazopyridine. Other drugs can be delivered in other embodiments.

In one example, the drug delivery portion is implanted by passing the drug delivery portion through a deployment instrument and releasing the device from the deployment instrument into the body. In cases in which the device is deployed into a body cavity such as the bladder, the drug deliver portion may assume a retention shape, such as an expanded or higher profile shape, once the drug delivery portion emerges from the deployment instrument into the cavity.

Once implanted, the drug delivery portion may release the drug. The drug delivery portion may provide extended, continuous, intermittent, or periodic release of a desired quantity of drug over a desired, predetermined time period. In embodiments, the drug delivery portion can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated. The deployed drug delivery portion may release one or more drugs for the treatment of one or more conditions, locally to one or more tissues at the deployment site and/or regionally to other tissues distal from the deployment site. The release may be controlled over an extended period. Thereafter, the drug delivery portion may be removed, resorbed, excreted, or some combination thereof.

In embodiments in which the drug delivery portion comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

Subsequently, the ureteral stent device and/or drug delivery portion may be retrieved from the body, such as in cases in which the drug delivery portion is non-resorbable or otherwise needs to be removed. Retrieval devices for this purpose are known in the art or can be specially produced. The drug delivery portion also may be completely or partially bioresorbable, such that retrieval is unnecessary, as either the entire drug delivery portion is resorbed or the drug delivery portion sufficiently degrades for expulsion from the bladder during urination. The drug delivery portion may not be retrieved or resorbed until some of the drug, or preferably most or all of the drug, has been released. If needed, a new drug-loaded device may subsequently be implanted, during the same procedure as the retrieval or at a later time.

In one embodiment, the implantable device, with a self-contained drug payload, is deployed wholly within the bladder to provide local, sustained delivery of at least one drug locally to the bladder in an effective amount. Following in-vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In one embodiment, the intravesical drug delivery portion is implanted into a bladder to locally deliver a local anesthetic agent for management of pain arising from any source, including but not limited to the deployment and/or presence of the ureteral stent, a disease or disorder in genitourinary tissues, or pain stemming from any bladder procedure, such as surgery, catheterization, ablation, medical device implantation, or stone or foreign object removal, among others. For example, a local anesthetic agent can be released into the bladder for regional delivery to nearby sites to manage nearby pain arising from any source, such as post-operative pain associated with the passage of a medical device into or through a ureter or other post-operative pain in sites apart from the bladder.

In one particular embodiment, a device having a payload of lidocaine may be delivered to the bladder, and lidocaine may be continuously released from the device over an extended period. In one embodiment, local delivery of lidocaine to the urothelium of the bladder is provided from the presently disclosed devices which have been deployed into the bladder in a manner which achieves a sustained level of lidocaine above the concentration that could be obtained for an extended period via instillation, yet without the high initial peak observed with instillation and without subsequent or associated significant systemic concentrations. In one embodiment, the device may have two payloads of lidocaine that are released at different times. The first payload may be adapted for relatively quick release, while the second payload may be adapted for more continuous release. For example, the first payload may be in liquid form or may be housed in a relatively fast-acting osmotic pump, such as a silicone tube having a relatively thinner wall, while the second payload may be solid form or may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device in which drug delivery may be delayed.

Methods of Deploying the Ureteral Stent Device

The ureteral stent device can be implanted in various manners. In some embodiments, the ureteral stent portion and the drug delivery portion may be deployed simultaneously. In other embodiments, the drug delivery portion may be deployed after the ureteral stent portion is deployed.

In an exemplary implantation procedure, the device may be deployed by threading the device over a guidewire extending through the ureter. An example of such an implantation procedure is illustrated in FIGS. 8A and 8B. A guidewire 596 may be threaded through a ureter 592 as shown in FIG. 8A such that the guidewire 596 extends from the bladder 590 to the kidney 594. The device then may be threaded over the guidewire, either with or without the assistance of a ureteral access sheath and/or a pusher. The guidewire is then removed from the ureter, leaving the ureteral stent device in position. In embodiments in which the stent device includes pigtail ends, the ends may return as shown in FIG. 8B to retain the stent in position. The central lumen 598 of the stent portion may extend through ureter 529 providing a path for the flow of urine from the kidney 594 to the bladder 590. In one embodiment, one end of the stent forms a pigtail 599 within the kidney and the drug delivery portion 597 forms a pigtail shape within the bladder 590.

In another implantation procedure, the guidewire may extend only through the stent portion and not the drug delivery portion. For example, as illustrated in FIG. 10, the drug delivery portion 614 may be tethered to the end of the stent portion 612 by a tether 616, such as a suture, and pulled behind the stent portion 612 as the stent portion is threaded over a guidewire 620 with the assistance of a pusher 618 and/or a access sheath (not shown) and deployed in the ureter. In such an embodiment, the drug delivery portion 614 may float freely in the bladder.

In yet another embodiment, the ureteral stent portion may be deployed by any known manner (e.g., with the use of a guidewire or access sheath) and the drug delivery portion may thereafter be deployed into the bladder, e.g., with the assistance of a catheter or cystoscope. Once both the ureteral stent portion and drug delivery portions are deployed into the ureter and bladder, respectively, the drug delivery portion may then be linked to bladder-residing end of the ureteral stent with an attaching element, such as a suture, mechanicallink, or magnets.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims While particular embodiments of ureteral stent devices are disclosed in detail in the foregoing description and figures for purposes of example, those skilled in the art will understand that variations and modifications may be made without departing from the scope of the disclosure. For instance, features illustrated or described as part of one embodiment can be used on another embodiment to yield a still further embodiment. All such variations and modifications are intended to be included within the scope of the present disclosure, as protected by the following claims and the equivalents thereof.

We claim:

1. An implantable medical device, comprising:
 a ureteral stent comprising an elongated central body having an internal lumen extending between a kidney-residing end and an opposed bladder-residing end of the ureteral stent; and
 a drug delivery component extending from the bladder-residing end of the ureteral stent, wherein the drug delivery component has a proximal end attached to the ureteral stent and a distal end spaced apart from the ureteral stent, wherein the drug delivery component comprises a drug housing defining a drug reservoir containing a drug in solid or semi-solid form, wherein the drug housing is configured to release the drug in vivo, and wherein the drug reservoir is fluidly separate and spaced apart from the internal lumen of the ureteral stent.

2. The implantable medical device of claim 1, wherein the bladder-residing end of the ureteral stent comprises a pigtail configuration.

3. The implantable medical device of claim 1, wherein:
 the drug housing comprises a tube; and
 the drug comprises a plurality of solid drug tablets aligned in a row in the tube.

4. The implantable medical device of claim 1, wherein the drug housing comprises a water-permeable material.

5. The implantable medical device of claim 1, wherein the drug housing comprises a silicone.

6. The implantable medical device of claim 1, wherein the drug housing is configured to release the drug in-vivo at a controlled rate for an extended period.

7. The implantable medical device of claim 1, wherein:
 the drug housing comprises a release aperture; and
 the drug comprises a water soluble salt form of lidocaine.

8. The implantable medical device of claim 1, wherein:
 the drug comprises a lidocaine base; and
 the drug housing comprises a material that is permeable to the lidocaine base.

9. The implantable medical device of claim 1, wherein the drug housing comprises a tube aligned with and attached to the bladder-residing end of the ureteral stent.

10. The implantable medical device of claim 1, wherein:
 the bladder-residing end of the ureteral stent comprises a pigtail configuration; and
 a portion of the drug delivery component is parallel and adjacent to the bladder-residing end of the ureteral stent.

11. The implantable medical device of claim 10, wherein the portion of the drug delivery component is configured to lie inside the bladder-residing end of the ureteral stent when in the pigtail configuration.

12. The implantable medical device of claim 1, wherein:
 the bladder-residing end of the ureteral stent comprises a pigtail configuration; and
 the drug delivery component extends from a distal tip of the bladder-residing end of the ureteral stent.

13. The implantable medical device of claim 12, further comprising a urine outflow aperture.

14. The implantable medical device of claim 1, wherein the drug delivery component is deformable between a retention shape and a deployment shape.

15. The implantable medical device of claim 14, wherein the drug delivery component comprises a retention frame operable to cause the drug delivery component to assume the retention shape upon deployment of the drug delivery component within the bladder.

16. The implantable medical device of claim 1, wherein the drug delivery component comprises a pigtail configuration.

17. The implantable medical device of claim 1, wherein the drug delivery component further comprises:
 a central lumen fluidly connected with the internal lumen of the ureteral stent; and
 a urine outflow aperture disposed at the distal end of the drug delivery component and in communication with the central lumen.

18. The implantable medical device of claim 1, wherein:
 the ureteral stent further comprises a urine outflow aperture disposed at or proximal to the bladder-residing end of the ureteral stent and in communication with the internal lumen of the ureteral stent; and the drug delivery component comprises a central lumen defining the drug reservoir.

19. The implantable medical device of claim 1, wherein the ureteral stent and the drug delivery component are formed separately and then attached to each other.

20. The implantable medical device of claim 1, wherein the ureteral stent and the drug delivery component are formed integrally as a single unit.

21. The implantable medical device of claim 1, wherein the proximal end of the drug delivery component is attached to a distal tip of the bladder-residing end of the ureteral stent.

22. The implantable medical device of claim 21, wherein a central axis of the proximal end of the drug delivery component is coaxial with a central axis of the bladder-residing end of the ureteral stent.

23. The implantable medical device of claim 1, wherein the bladder-residing end of the ureteral stent comprises a straight configuration, and wherein the drug delivery component comprises a pigtail configuration.

24. The implantable medical device of claim 1, wherein the drug reservoir comprises an annular shape.

25. The implantable medical device of claim 24, wherein the drug delivery component further comprises a central lumen extending through the drug reservoir.

26. The implantable medical device of claim 1, wherein the drug comprises a chemotherapeutic agent.

27. The kit of claim 26, wherein the drug comprises a chemotherapeutic agent.

28. A method of delivering a drug from a ureteral stent device, comprising:
    implanting a ureteral stent device in a ureter of a patient to maintain patency of the ureter, the ureteral stent device comprising:
        a ureteral stent comprising an elongated central body having an internal lumen extending between a kidney-residing end and an opposed bladder-residing end of the ureteral stent; and
        a drug delivery component extending from the bladder-residing end of the ureteral stent, the drug delivery component having a proximal end attached to the ureteral stent and a distal end spaced apart from the ureteral stent, the drug delivery component comprising a drug housing defining a drug reservoir containing a drug in solid or semi-solid form; and
    releasing the drug from the drug housing into the patient's body.

29. The method of claim 28, wherein the drug is selected from the group consisting of: a local anesthetic agent, an anti-muscarinic, an alpha-blocker, a narcotic, phenazopyridine, an antibiotic, an anticholinergic, and combinations thereof.

30. The method of claim 29, wherein the drug is a local anesthetic agent, which is lidocaine.

31. The method of claim 28, wherein the drug is a drug effective to treat urinary tract cancer.

32. A method of treating one or more side effects associated with placement of a ureteral stent in the body of a patient, comprising:
    implanting a ureteral stent device in a ureter of a patient to maintain patency of the ureter, the ureteral stent device comprising:
        a ureteral stent comprising an elongated central body having an internal lumen extending between a kidney-residing end and an opposed bladder-residing end of the ureteral stent; and
        a drug delivery component extending from the bladder-residing end of the ureteral stent, the drug delivery component having a proximal end attached to the ureteral stent and a distal end spaced apart from the ureteral stent, the drug delivery component comprising a drug housing defining a drug reservoir containing a drug in solid or semi-solid form; and
    releasing the drug from the drug housing into the patient, the drug being selected from the group consisting of: a local anesthetic agent, an anti-muscarinic, an alpha-blocker, a narcotic, phenazopyridine, and combinations thereof.

33. The method of claim 32, wherein the drug comprises lidocaine.

34. The method of claim 32, wherein the drug is a drug effective to treat urinary tract cancer.

35. A medical procedure kit comprising:
    a ureteral stent comprising an elongated central body having an internal lumen extending between a kidney-residing end and an opposed bladder-residing end of the ureteral stent;
    at least one drug delivery component having a proximal end with means for attachment to the bladder-residing end of the ureteral stent in-vivo such that the drug delivery component extends from the bladder-residing end and a distal end of the drug delivery component is spaced apart from the ureteral stent, wherein the drug delivery component comprises a drug housing defining a drug reservoir containing a drug in solid or semi-solid form, wherein the drug housing is configured to release the drug in vivo, and wherein the drug reservoir is fluidly separate and spaced apart from the internal lumen of the ureteral stent.

36. The kit of claim 35, further comprising one or more of a guidewire, a dilator, and a deployment sheath.

* * * * *